United States Patent [19]
Kriesel

[11] Patent Number: 5,743,879
[45] Date of Patent: Apr. 28, 1998

[54] MEDICAMENT DISPENSER

[75] Inventor: Marshall S. Kriesel, Saint Paul, Minn.

[73] Assignee: Science Incorporated, Bloomington, Minn.

[21] Appl. No.: 473,650

[22] Filed: Jun. 6, 1995

Related U.S. Application Data

[63] Continuation-in-part of Ser. No. 349,496, Dec. 2, 1994.

[51] Int. Cl.$^6$ .................................................. A61M 37/00
[52] U.S. Cl. ......................... 604/132; 604/131; 604/157; 128/DIG. 12
[58] Field of Search ..................... 604/131, 132, 604/134, 135, 140, 141, 184, 185, 151; 128/DIG. 12

[56] References Cited

U.S. PATENT DOCUMENTS

| | | |
|---|---|---|
| 2,995,373 | 3/1961 | Cox . |
| 4,209,014 | 6/1980 | Sefton ............................ 128/214 F |
| 4,592,745 | 6/1986 | Rex ................................. 604/211 |
| 4,636,197 | 1/1987 | Chu ............................. 128/DIG. 12 |
| 4,813,937 | 3/1989 | Vaillancourt ..................... 604/131 |
| 4,950,163 | 8/1990 | Zimble ............................ 433/215 |
| 5,019,047 | 5/1991 | Kriesel ............................ 604/132 |
| 5,024,662 | 6/1991 | Menes et al. .................... 604/131 |
| 5,041,094 | 8/1991 | Perego ........................ 128/DIG. 12 |
| 5,078,679 | 1/1992 | Reese ............................... 604/51 |
| 5,084,021 | 1/1992 | Baldwin ........................... 604/131 |
| 5,100,389 | 3/1992 | Vaillancourt ..................... 604/135 |
| 5,429,607 | 7/1995 | McPhee .......................... 604/131 |

*Primary Examiner*—Sam Rimell
*Assistant Examiner*—Luke Yeh
*Attorney, Agent, or Firm*—James E. Brunton

[57] ABSTRACT

An injectable medicament dispenser for use in controllably dispensing fluid medicaments such as insulin, antibiotics, oncolytics and the like from a prefilled container at a uniform rate. The dispenser includes a unique stored energy source in the form of a compressively deformable, polymeric elastomeric member that provides the force necessary to controllably discharge the medicament from the prefilled container which is housed within the body of the device. After having been deformed, the polymeric, elastomeric member will return to its starting configuration in a highly predictable manner.

17 Claims, 14 Drawing Sheets

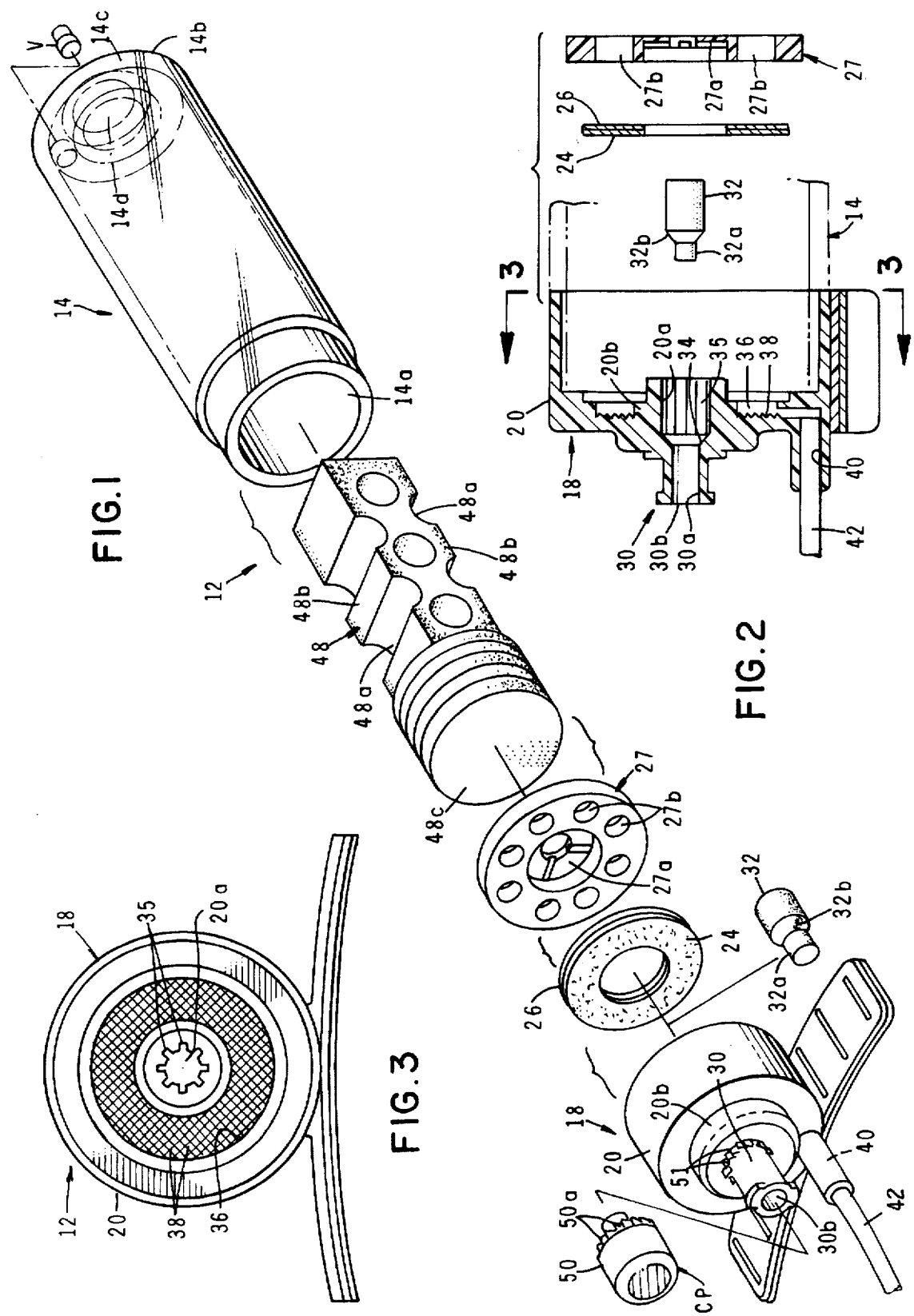

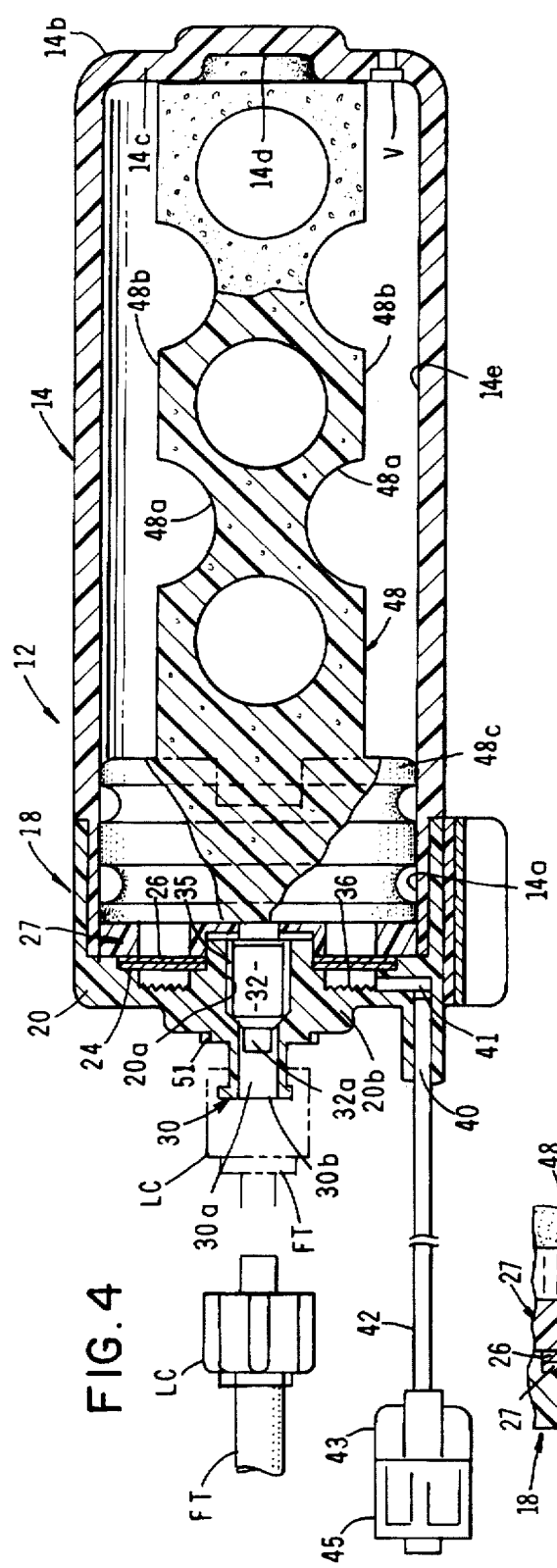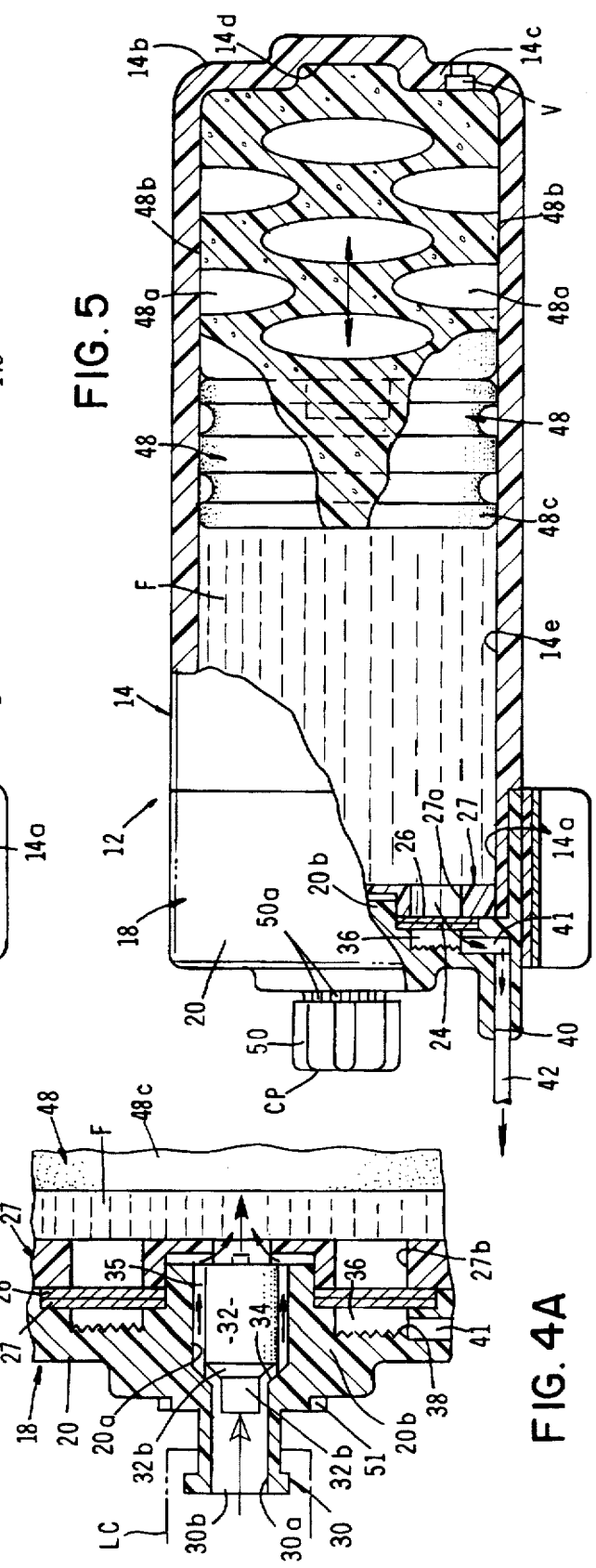

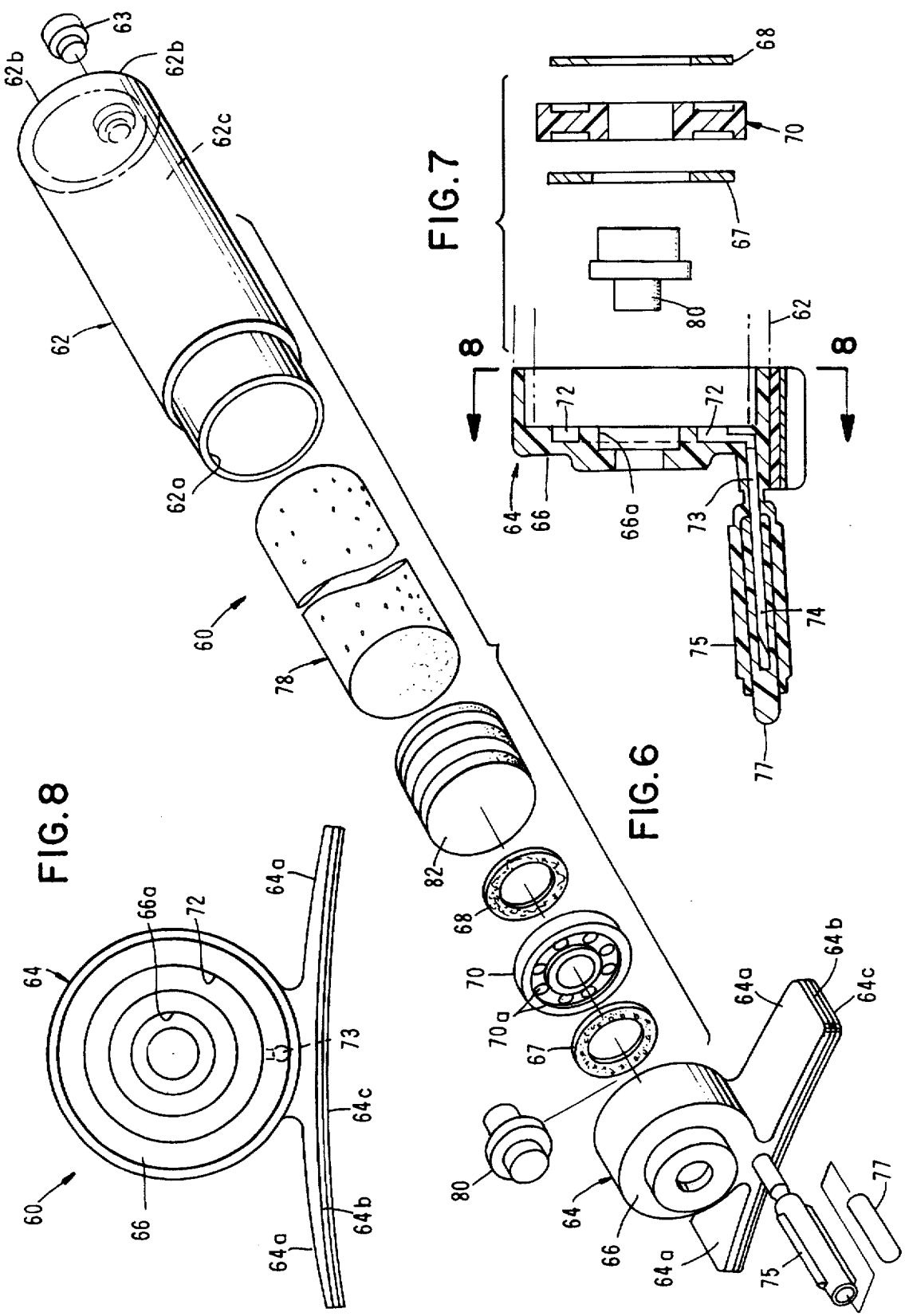

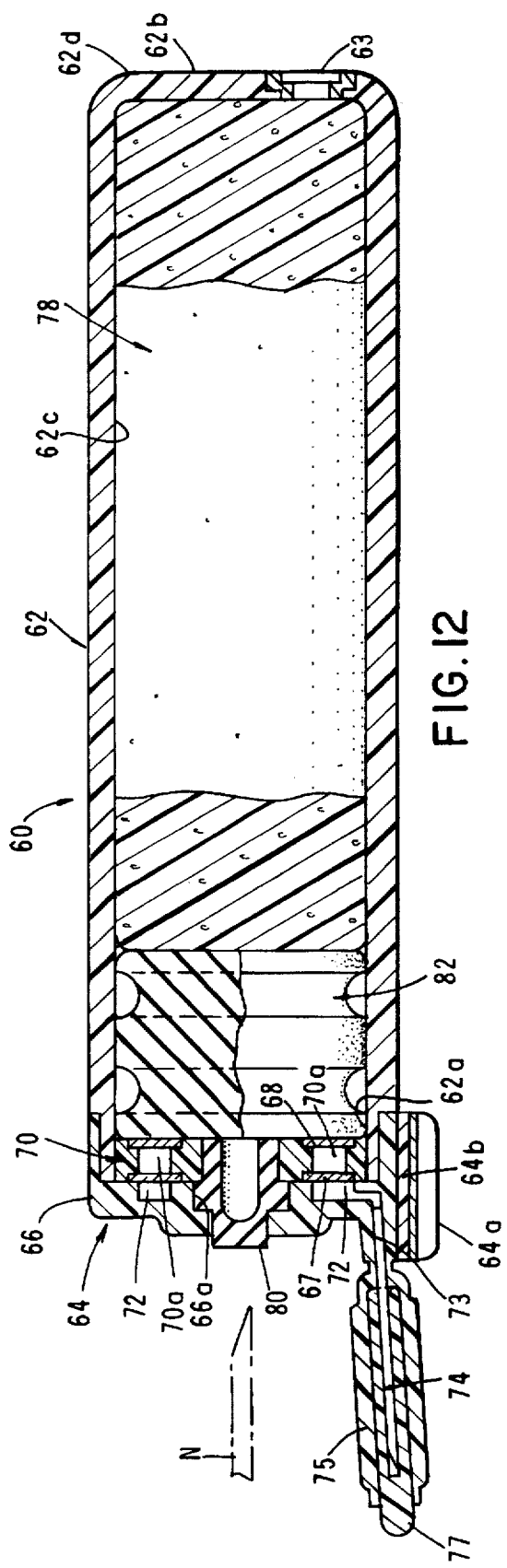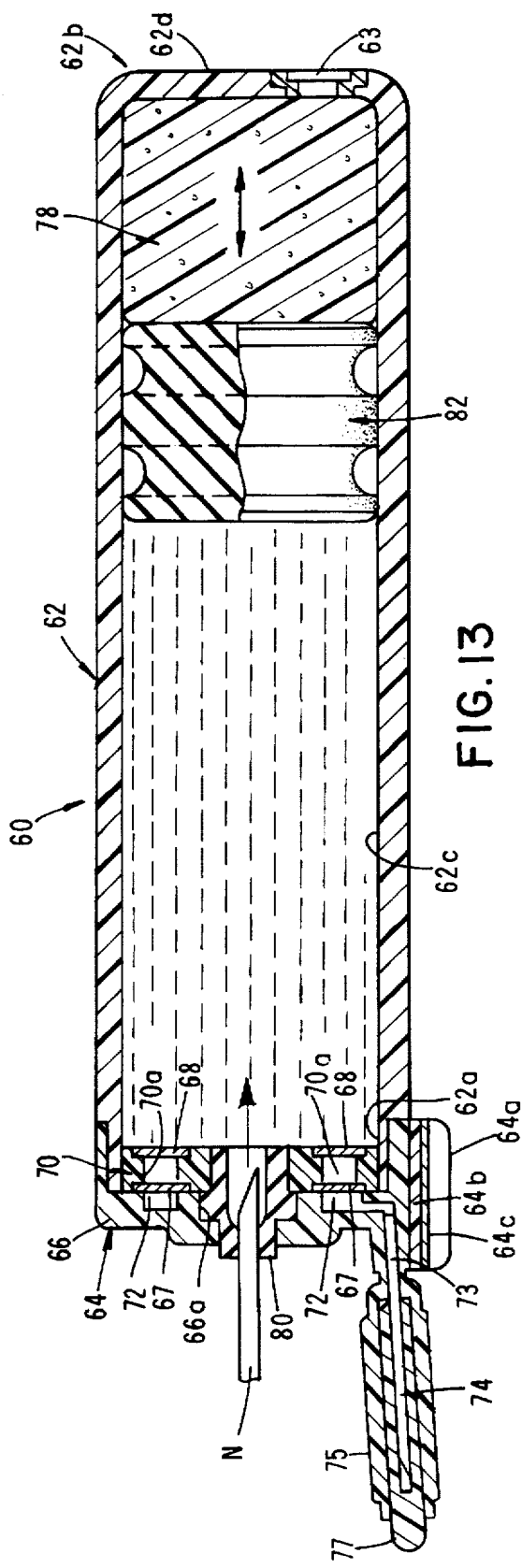

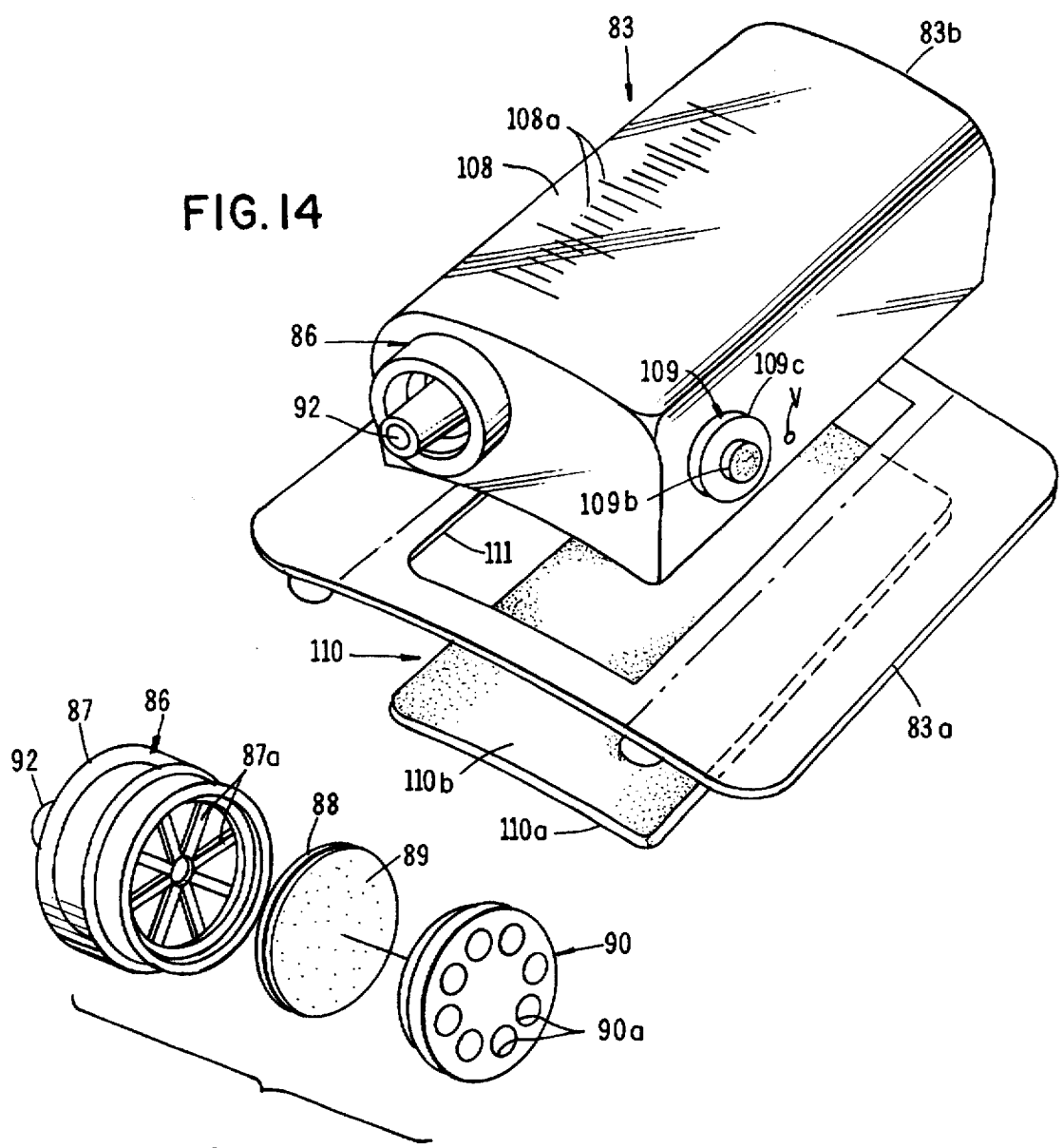
FIG. 14
FIG. 17
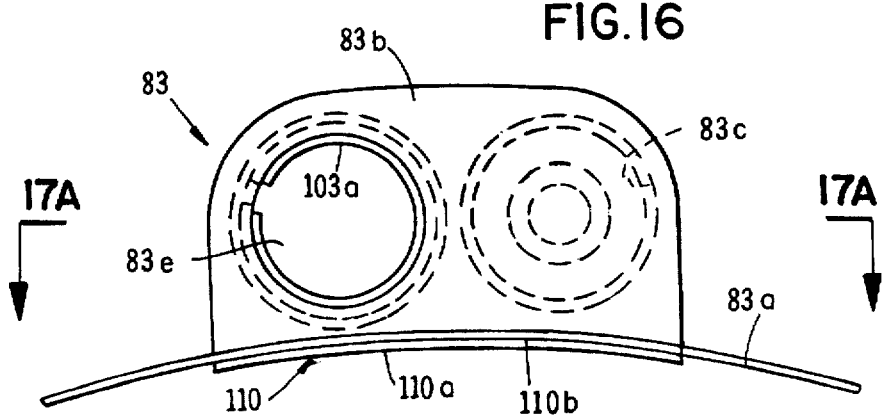
FIG. 16

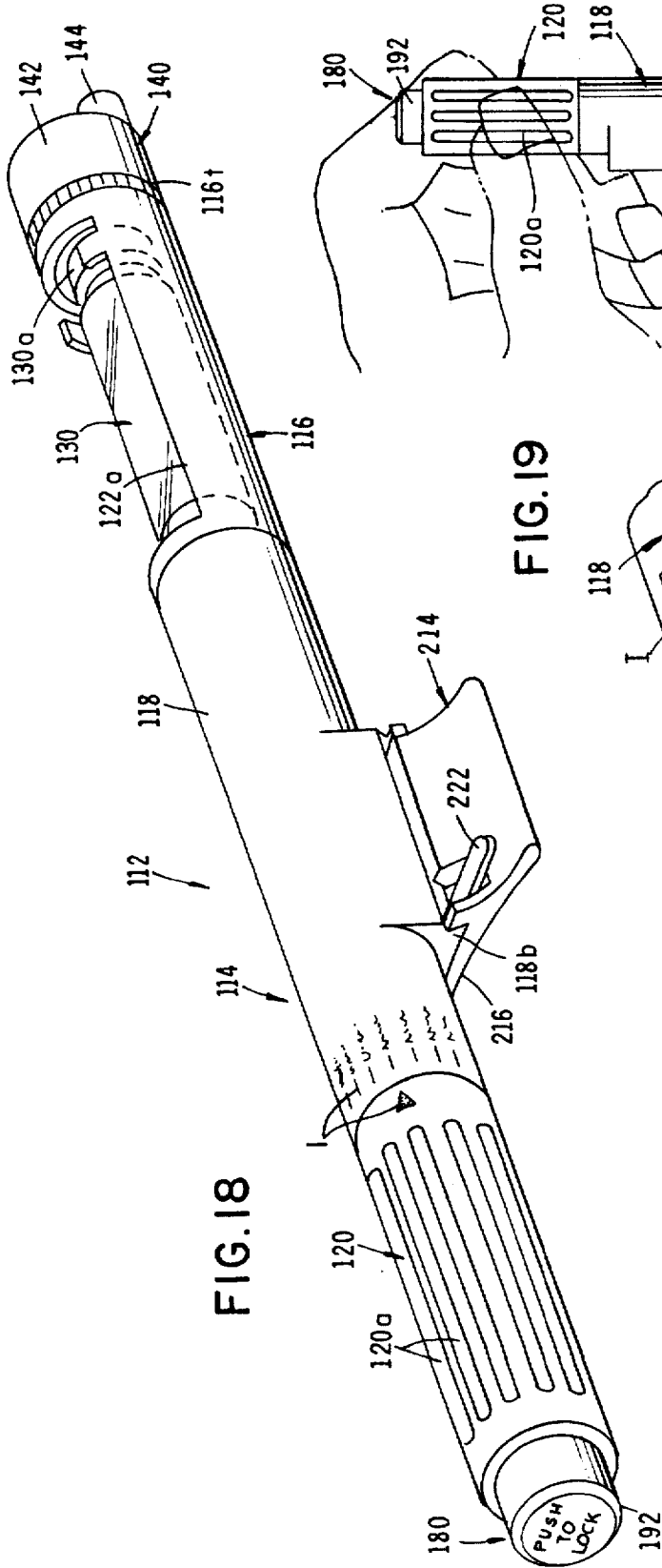
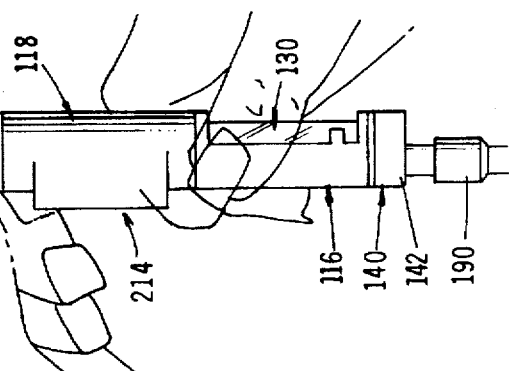
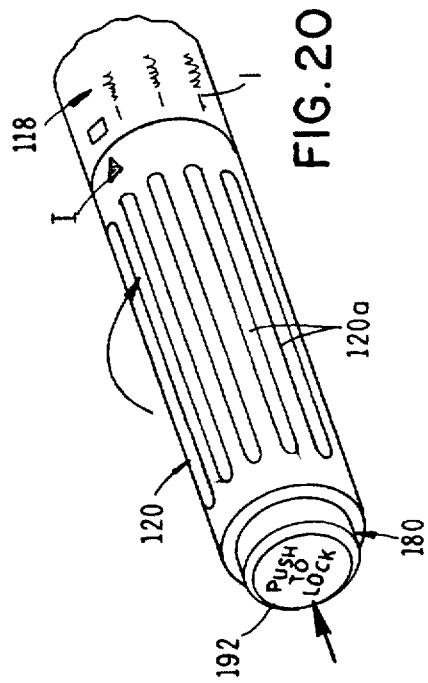
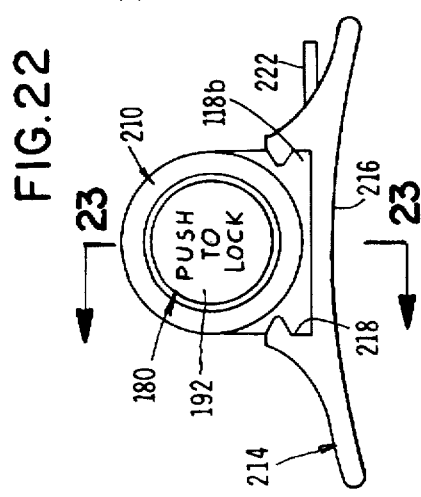

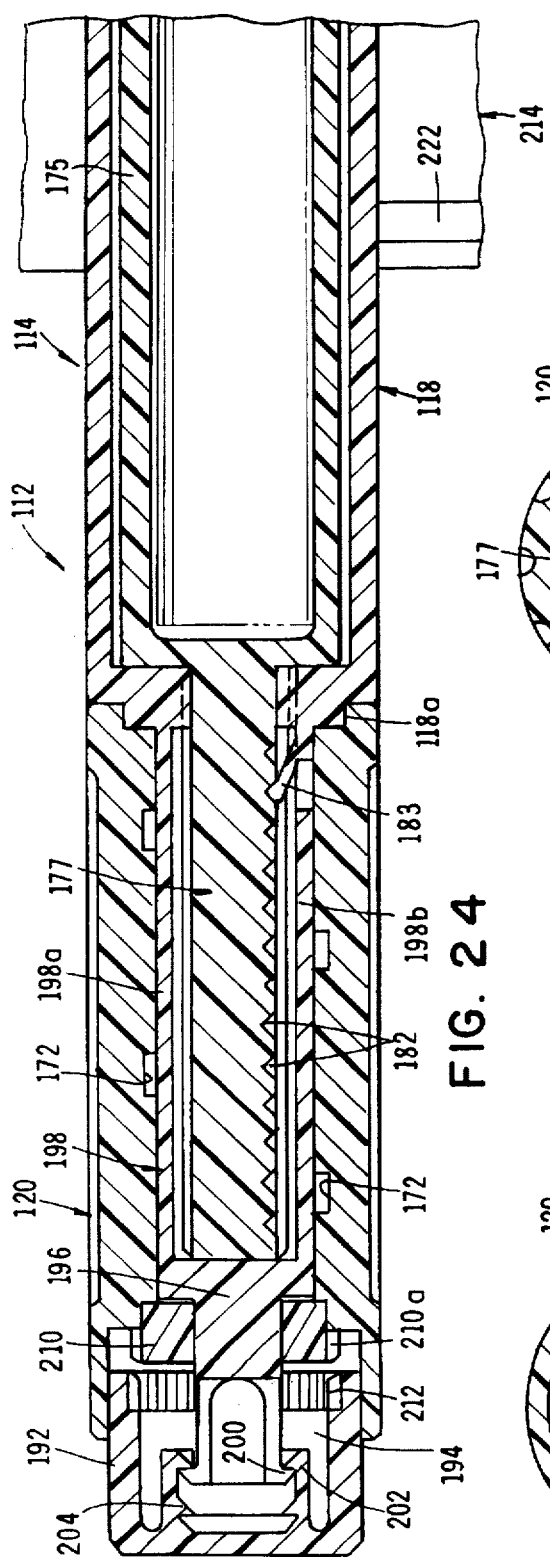
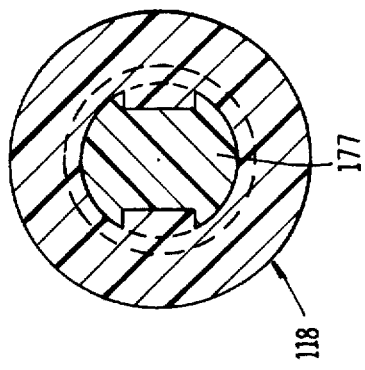
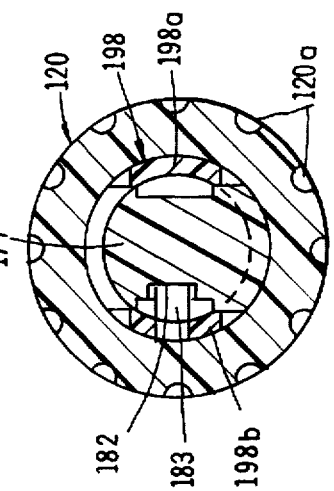
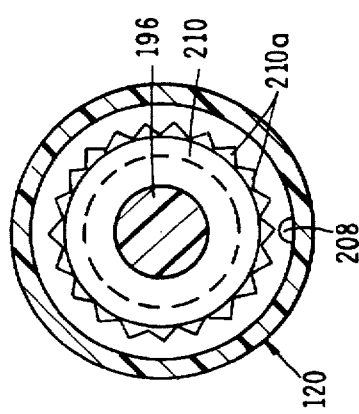
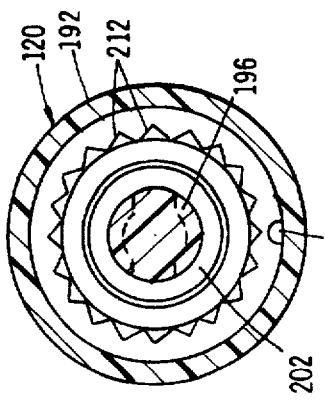

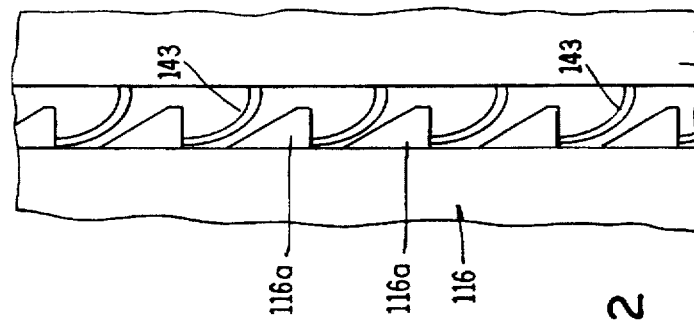
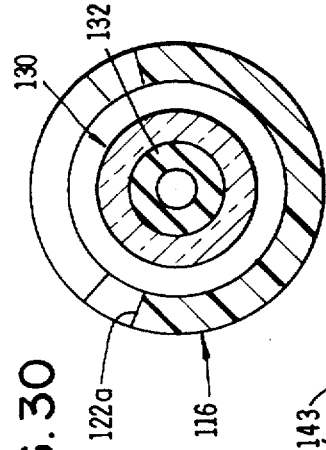
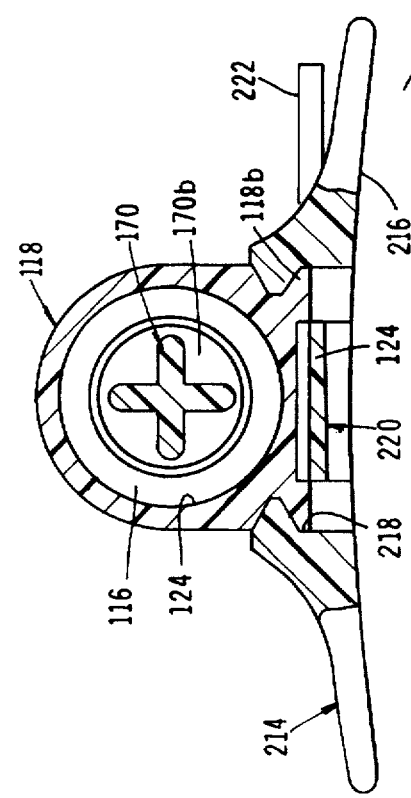
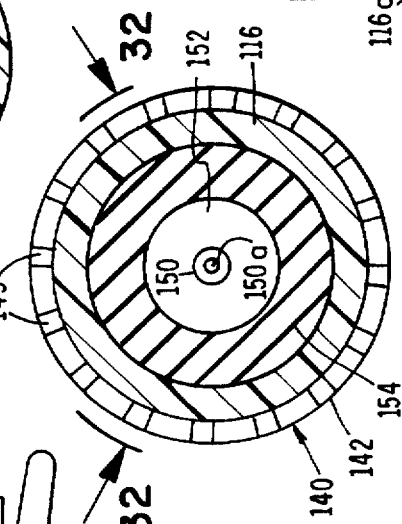
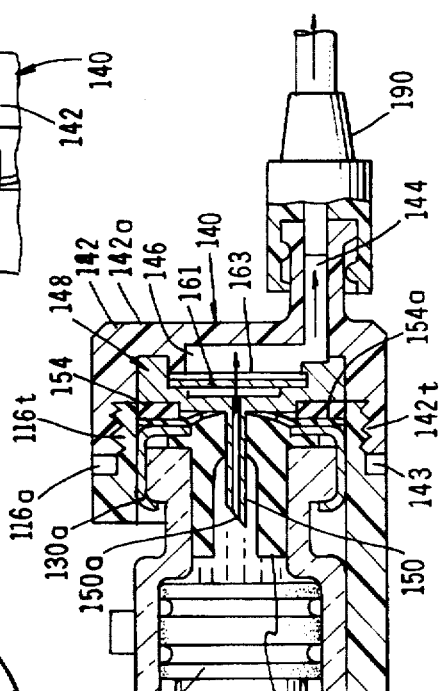
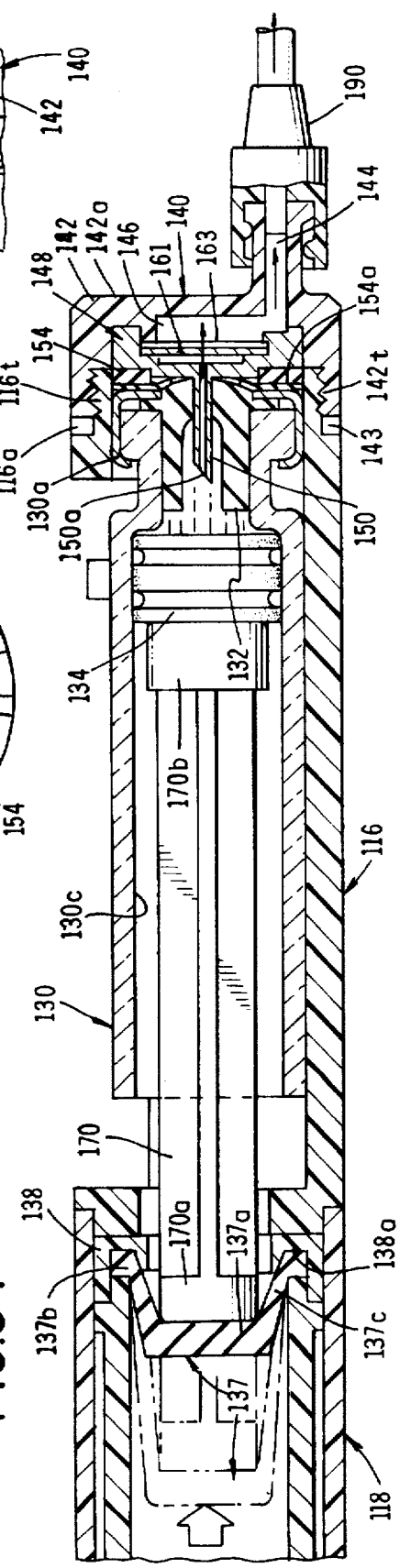

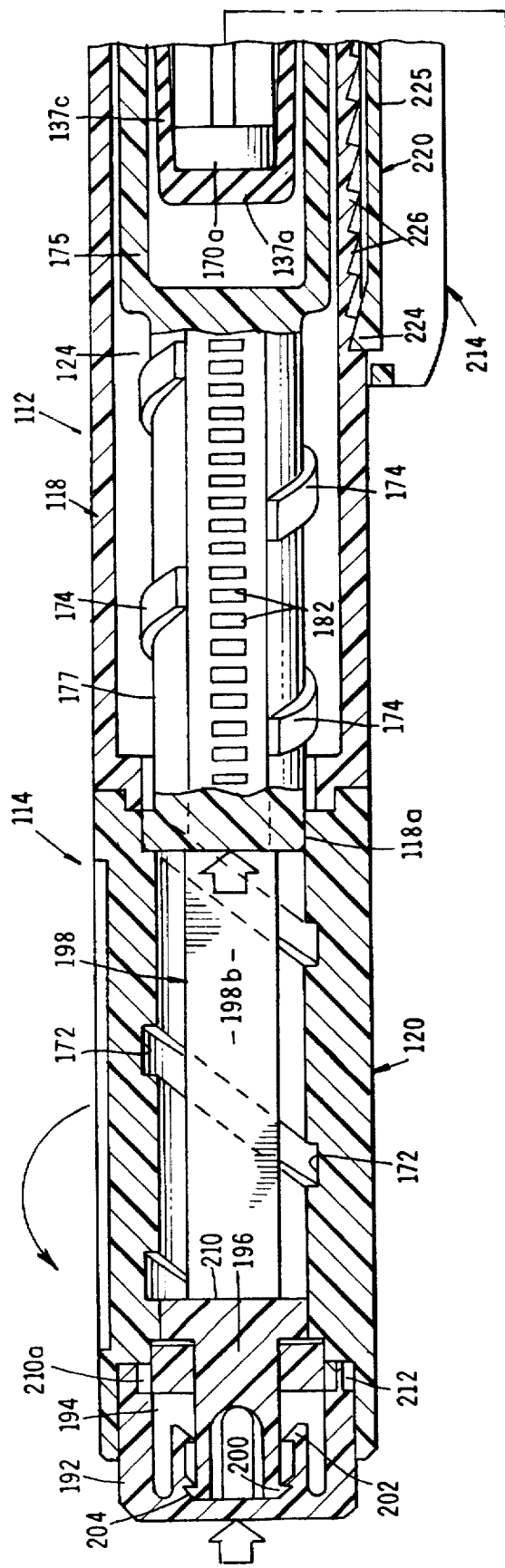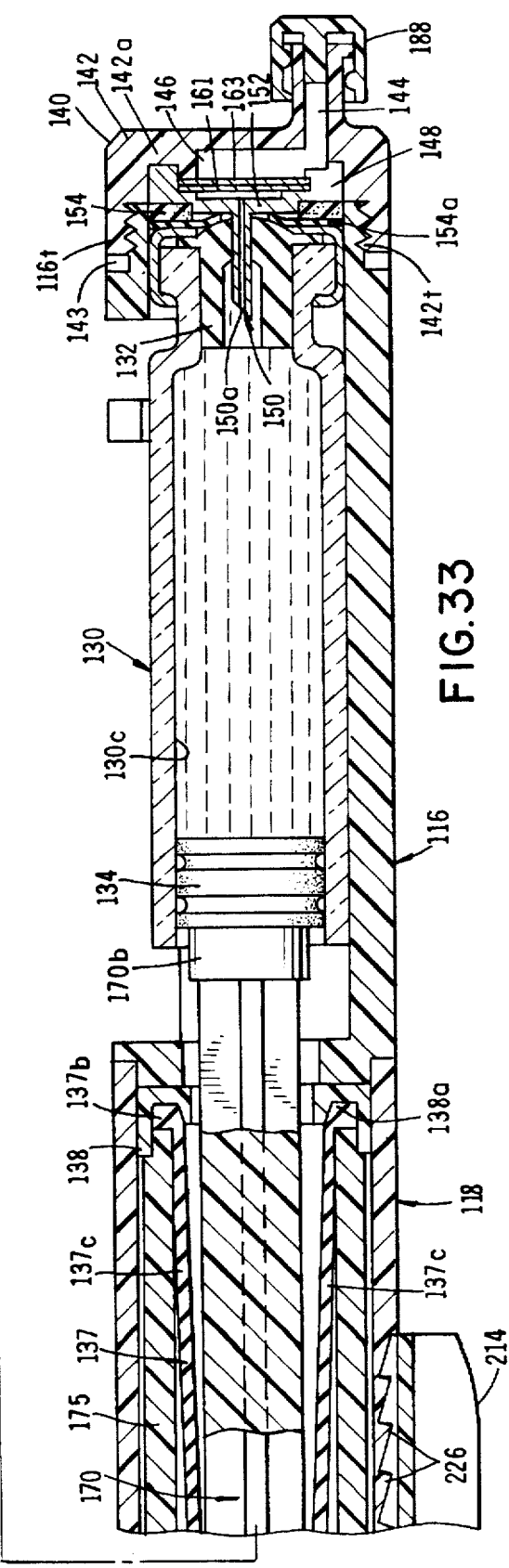
FIG.33

MEDICAMENT DISPENSER

This is a Continuation-In-Part of co-pending application Ser. No. 08/349,496 filed Dec. 2, 1994.

BACKGROUND OF THE INVENTION

1. Field of the Invention

The present invention relates generally to fluid medicament dispensers. More particularly, the invention concerns a dispenser for use in controllably dispensing a liquid medicament as, for example, an insulin solution.

DISCUSSION OF THE INVENTION

Traditionally, conventional syringes are used to inject many beneficial agent solutions such as insulin. In accordance with conventional procedures, the prescribed dose is first drawn into the syringe and a visual check is made to make certain that the correct amount of insulin is present in the syringe. Next, air is expelled from the syringe and the dose is injected manually.

These conventional procedures have numerous drawbacks including adverse reaction caused by the bolus injection of drugs by hand via a syringe. In the majority of cases, the adverse reactions are not due to the drug itself, but rather are due to an improper rate of injection of the drug. Ideally, the contents of a syringe should be delivered over a number of minutes or hours. However, in clinical practice, this rarely occurs due to time pressure on the staff who must operate the syringe manually.

Because diabetics generally require regular and repeated injections of insulin, the use of self-delivering devices, such as conventional syringes, is cumbersome, time consuming, and dangerous if not properly performed. In addition, the process of sticking one's self and expulsing the liquid medicament can be extremely unpleasant for the medically untrained. For this reason, several types of dispensing devices have been suggested for automatically dispensing a predetermined quantity of a liquid medicament such as insulin from a multi-dose container. Exemplary of such devices are those described in European Patent Application No. 37696 and in U.S. Pat. No. 4,592,745 issued to Rex, et al. Both of the aforementioned devices dispense a predetermined quantity of liquid from a liquid reservoir or container and both include mechanical operating mechanisms for expelling the fluid from the reservoir.

The Rex, et al device comprises an elongated body formed from two separable sections one of which contains an operating mechanism and the other of which contains a prefilled cartridge. The operating mechanism of the device mechanically advances an axially movable piston rod which, in turn, drives a piston plug located inside the cartridge so as to expel fluid from the device via a needle located at the bottom end of the body. The piston rod advances in successive axial steps of fixed length through rotation of a rotatable piston rod nut. The piston rod nut is driven by a rotatable worm, which is rotated by the advancing axial movement of a pressure device located at the top of the elongated body.

The EPO application discloses a dispensing device somewhat similar to the Rex, et al. device, but embodies an operating mechanism that comprises a pawl which permits relative movement of a ratchet-toothed member in a substantially rectilinear arrangement. As in the Rex, et al. device, the operating mechanism drives the plunger of a medicament vial to expel fluid therefrom.

U.S. Pat. No. 4,813,937 issued to Vaillancourt discloses an infusion system in which the inflow of fluid into the device causes an elastomeric member attached to a piston to be moved so as to stretch the elastomeric member. The thusly tensioned elastomeric member provides the source of energy to expel the fluid from the device when the outlet tubing of the system is opened. However, as is clear from a study of the Vaillancourt patent, the device disclosed therein operates in a substantially different manner than the device of the present invention.

Electrically operated syringe pumps are also well known, however, they are typically of considerable complexity and are designed to inject very small doses of medicine with considerable accuracy over a long period, which may be up to 24 hours. Such syringe pumps do not provide the inexpensive, simple and manually operated device suitable for the slow injection of drugs over a shorter period of time, which may range from one to 15 minutes.

Many of the prior art medicament dispensing devices are of complex construction and, therefore, are often very expensive to manufacture. Additionally, such devices tend to be somewhat unreliable in use and frequently have a limited useful life. In using certain of the prior art devices, maintaining sterility has also proven to be a problem.

As will be appreciated from the discussion which follows, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a constant-force spring that provides the force necessary to uniformly and precisely dispense solutions, such as insulin, from standard prefilled containers that can be conveniently loaded into the apparatus. Because of the simplicity of construction of the apparatus of the invention, and the straight-forward nature of the energy source, the apparatus can be manufactured at low cost without in any way sacrificing accuracy and reliability.

A somewhat similar medicament dispenser is disclosed in co-pending application Ser. No. 08/349,496 filed by the present inventor. This application is hereby incorporated herein by reference as though fully set forth herein. Reference to this earlier-filed application will show that the device of the present invention embodies a stored energy means of quite a different construction and mode of operation than that disclosed in Ser. No. 08/349,496.

SUMMARY OF THE INVENTION

It is an object of the present invention to provide a small, compact fluid dispenser for use in controllably dispensing fluid medicaments, such as insulin, antibiotics, oncolytics and the like from a prefilled container at a uniform rate.

Another object is to provide a device of the aforementioned character which is of very simple construction and embodies a minimum number of parts.

Another object of the invention is to provide a small, compact fluid dispenser that is receivable within a housing to which a fill vial can be connected for filling the dispenser with the fluid.

Another object of the invention is to provide a dispenser in which a stored energy source is provided in the form of a stretchable, elastomeric member of novel construction that provides the force necessary to continuously and uniformly expel fluid from the prefilled container.

Another object of the invention is to provide a dispenser of the character described in the preceding paragraph in which the elastomeric member is uniformly and controllably stretched by a novel stretching mechanism and, after being stretched, exhibits a tendency to predictably return toward it original configuration.

Another object of the invention is to provide a dispenser of the class described which includes a fluid flow control assembly that filters and precisely controls the flow of the medicament solution from the prefilled container.

Another object of the invention is to provide a fluid dispenser which is adapted to be used with conventional prefilled insulin drug vials to deliver an insulin solution therefrom in a precise and sterile manner.

Another object of the invention is to provide a fluid dispenser of the class described which is compact, lightweight, is easy for ambulatory patients to use, is fully disposable, and is extremely accurate so as to enable the infusion of precise doses of insulin over prescribed periods of time.

Another object of the invention is to provide a self-contained medicament dispenser which is of very simple construction and yet extremely reliable in use.

Another object of the invention is to provide a dispenser of the class described which includes means for interconnecting the device with the body or clothing of the patient.

Another object of the invention is to provide a fluid dispenser as described in the preceding paragraphs which is easy and inexpensive to manufacture in large quantities.

BRIEF DESCRIPTION OF THE DRAWINGS

FIG. 1 is a generally perspective, exploded view of one embodiment of the dispensing apparatus of the present invention for dispensing fluids at a uniform rate.

FIG. 2 is a cross-sectional, exploded view of the dispensing head portion of the apparatus of FIG. 1.

FIG. 3 is a view taken along lines 3—3 of FIG. 2.

FIG. 4 is an enlarged, side-elevational, cross-sectional view of the assembled apparatus of the form of the invention shown in FIG. 1.

FIG. 4A is an enlarged, side-elevational, cross-sectional view of the forward portion of the apparatus illustrating the appearance of the various components during the filling step.

FIG. 5 is an enlarged side-elevational view similar to FIG. 4, but showing the apparatus filled with the fluid to be dispersed.

FIG. 6 is a generally perspective, exploded view of an alternate embodiment of the dispensing apparatus of the present invention for dispensing fluids at a uniform rate.

FIG. 7 is a fragmentary, cross-sectional, exploded view of the forward portion of the apparatus including the dispensing head.

FIG. 8 is a view taken along lines 8—8 of FIG. 7.

FIG. 12 is an enlarged, side-elevational view of the assembled apparatus of the form of the invention shown in FIG. 6.

FIG. 13 is an enlarged, side-elevational view similar to FIG. 12, but showing the apparatus filled with the fluid to be dispersed.

FIG. 14 is a generally perspective, exploded view of still another embodiment of the dispensing apparatus of the present invention for dispensing fluids at a uniform rate.

FIG. 16 is a right end view of the apparatus shown in FIG. 14.

FIG. 17 is an enlarged, generally perspective exploded view of the fluid dispensing head and flow control means of this latest form of the invention.

FIG. 18 is a generally perspective view of still another embodiment of the dispensing apparatus of the present invention for dispensing fluids at a uniform rate.

FIG. 19 is a generally perspective, diagrammatic view illustrating the manner in which a portion of the operating member of the apparatus is advanced by the user into the body of the apparatus.

FIG. 20 is a fragmentary, generally perspective view of the left-end portion of the apparatus shown in FIG. 18 illustrating rotational movement of the end portion and further illustrating the direction of the force necessary to operate the locking mechanism of the device.

FIG. 22 is an enlarged, left-end view of the apparatus shown in FIG. 1.

FIG. 24 is a cross-sectional view taken along lines 24—24 of FIG. 23.

FIG. 25 is a cross-sectional view taken along lines 25—25 of FIG. 23.

FIG. 26 is a cross-sectional view taken along lines 26—26 of FIG. 23.

FIG. 27 is a cross-sectional view taken along lines 27—27 of FIG. 23.

FIG. 28 is a cross-sectional view taken along lines 28—28 of FIG. 23.

FIG. 29 is a cross-sectional view taken along lines 29—29 of FIG. 23.

FIG. 30 is a cross-sectional view taken along lines 30—30 of FIG. 23.

FIG. 31 is a cross-sectional view taken along lines 31—31 of FIG. 23.

FIG. 32 is a development view taken along lines 32—32 of FIG. 31 illustrating the manner in which the locking teeth and locking tabs of the device cooperate to lock the operating member to the housing.

FIG. 33 is an enlarged, cross-sectional view similar to FIG. 23, but showing the position of the component parts of the apparatus after a portion of the operating member has been threadably advanced into the body.

FIG. 34 is a fragmentary, cross-sectional view of the dispensing end portion of the apparatus illustrating the position of the cooperating component parts after the cannula has pierced the pierceable septum of the medicament vial.

DESCRIPTION OF THE INVENTION

Figure 9:
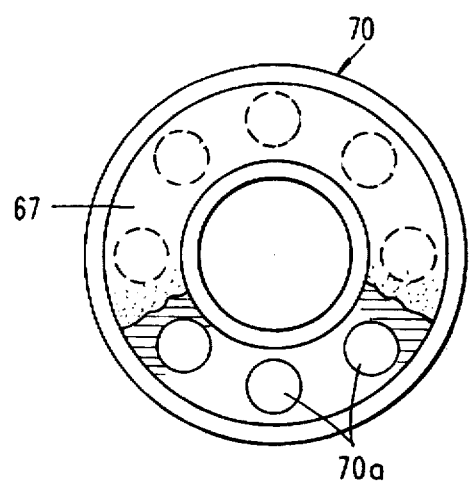
FIG. 9 is a view of the rate control element side of fluid flow control assembly of the apparatus.

Referring to the drawings and particularly to FIGS. 1 through 5, one embodiment of the medicament delivery system of the present invention is there illustrated and generally designated by the numeral 12. This embodiment is somewhat similar to that described in the parent application Ser. No. 08/349,496 which is incorporated by reference. However, the forms of the invention shown herein are quite small, very compact, easy to use, and are of a less complex construction than those illustrated and described in the parent application.

The apparatus of this latest form of the invention comprises a container 14, having a first open end 14a and a closed end 14b. End 14b is closed by an end wall 14c having a centrally disposed socket like portion 14d and a vent "V" for venting the interior of the container to atmosphere. Received within a reservoir-defining chamber 14e of container 14 is the stored energy means of this form of the invention, the purpose of which will presently be described.

First end 14a of the container is closed by a fill and dispensing means for filling chamber 14e with fluid and for dispensing fluid therefrom. The fill and dispensing means here comprises a dispensing head assembly generally designated by the numeral 18. As best seen in FIG. 2, assembly 18 includes a closure cap 20 which is receivable over container 14 in the manner shown in FIGS. 4 and 5. Disposed within cap 20 is a flow control means for controlling the outward flow of fluid flowing from the reservoir or internal chamber 14e of container 14. The flow control means of this embodiment of the invention comprises a generally annular shaped flow rate control element 24 and a generally annular shaped filter element 26. The flow control means further includes valve means which are supported within head assembly 18 by an apertured support 27 which supports the laminate made up of elements 24 and 26 and a bore 20a provided in the forward wall 20b of cap 20 (see FIG. 4). In a manner presently to be described, the valve means functions to block fluid flow between reservoir 14e and the fluid passageway 30a of a luer connector 30 which extends outwardly from wall 20b of cap 20 and defines the fluid inlet 30b of the device. The valve means here comprises a valve member 32 having a neck portion 32a and a seat engaging portion 32b which sealably engages a valve seat 34 formed internally of bore 20a.

Turning to FIGS. 3 and 4A it is to be noted that bore 20a includes a plurality of circumferentially spaced bypass flow channels 35 which permit fluid flow into reservoir 14e when valve member 32 is moved rearwardly away from seat 34 in the manner shown in FIG. 4A. As seen in FIG. 3, cap 20 is provided with an annular collector manifold 36 having micro-channels 38 that direct fluid flow from reservoir 14e toward the outlet port 40 of the device via a fluid passageway 41. Connected to outlet port 40 is a delivery conduit 42 having at its outboard end a male luer fitting 43 which mates with a female luer cap 45.

Disposed within reservoir 14e of the container 14 is the important stored energy means of the invention, which functions to urge fluid contained within the reservoir outwardly of the device via the flow control means. This unique stored energy means here comprises a specially configured elastomeric spring-like member 48 which is movable from a first configuration shown in FIG. 4 to a second, more compressed configuration shown in FIG. 5 wherein it has a tendency to return toward its first configuration. As best seen in FIG. 1, member 48 comprises an elongated compressible member having a plurality of longitudinally spaced apart grooves and ridges 48a and 48b respectively.

As discussed in U.S. Ser. No. 08/349,496, which is incorporated herein by reference, the stored energy means can be constructed from a wide variety of materials including rubbers, plastics and other thermoplastic elastomers (TPE) and thermoplastic urethane (TPU). By way of example, suitable materials include latex rubber, rubber polyolefins, polyisoprene (natural rubber), butyl rubber, nitrile rubber, polyurethane, vinyls, vinyl-end-blocked polydimethylsiloxanes, other homopolymer, copolymers (random alternating, block, graft, cross-link and star block), silicones and other flouropolymers, mechanical polyblends, polymer alloys and interpenetrating polymer networks.

In operating the apparatus of the form of the invention shown in FIG. 1 through 5, with the outlet conduit 42 closed by luer closure cap 45 (FIG. 4), a suitable filling tube "FT" and luer connector "LC" (FIG. 4) is interconnected with luer fitting 30 to enable filling of reservoir 14e with the fluid to be dispensed. During filling, valve member 32 will move away from seat 34 and into engagement with a central wall portion 27a provided on support 27 (FIG. 2) thereby permitting fluid to flow from the fill tube past valve member 32 via bypass channels 33 and into reservoir 14e.

As the fluid under pressure flows through bypass channels 35, and into reservoir 14e, it will engage the forward piston-like portion 48c of the stored energy member 48 urging portion 48c inwardly of reservoir 14e. As the fluid under pressure urges piston portion 48a telescopically of the reservoir, the body portion of the stored energy member will be compressed in the manner indicated in FIG. 5. When fluid flow ceases through fill tube 52, check valve member 32 will be urged by the fluid pressure within reservoir 14e into seating engagement with valve seats 34 thereby sealing the inlet port of the device so that the fluid "F" which is to be dispensed will be contained within reservoir 14e.

Following the filling step, a closure plug assembly "CP" is connected with luer fitting 30 so as to sealably close inlet 30b. As best seen in FIG. 1, closure plug assembly "CP" comprises a cap 50 which includes a multiplicity of circumferentially spaced locking fins 50a which are lockably received within a multiplicity of circumferentially spaced locking tabs 51 provided on assembly 18 (FIG. 1). With this construction, following filling, cap assembly "CP" is locked to assembly 18.

Upon opening the fluid delivery path by removal of closure cap 45 (FIG. 4), the stored energy means, or member 48, will tend to return to its uncompressed starting configuration thereby controllably urging fluid flow outwardly of the device via apertures 27b in support 27, via rate control element 24 and via filter element 26. Fluid flowing through these elements will flow into annular shaped fluid collection passageway 36 and then outwardly of the device via the delivery tube 42. Filter 26 which functions to filter particulate matter from the fluid flowing outwardly from reservoir 14e is of a character well known to those skilled in the art and can be constructed from various readily available materials such as polysolfone and polypropylene wafers having a desired porosity. Similarly, rate control element 24 can be constructed from any suitable porous material such as polycarbonate, a metal or a ceramic having the desired porosity.

As before various fluids can be dispensed from container 14, including, by way of example, beneficial agents such as medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Turning next to FIGS. 6 through 13 of the drawings, still another form of the dispensing apparatus of the present invention is there illustrated and generally designated by the numeral 60. The apparatus of this alternate form of the invention is also similar in certain respects to the previously described embodiments of the invention.

The apparatus of this latest form of the invention, like the embodiment just described, comprises a container 62, having a first open end 62a and a closed end 62b and a fluid reservoir 62c disposed between ends 62a and 62b. End 62b is closed by an end wall 62d provided with a gas vent 63 for venting any gases contained within reservoir 62c to atmosphere. Vent 63 can be constructed of a suitable porous material such as a porous plastic. Received within reservoir 62c is the stored energy means of this form of the invention, the character of which will presently be described.

Figure 10:
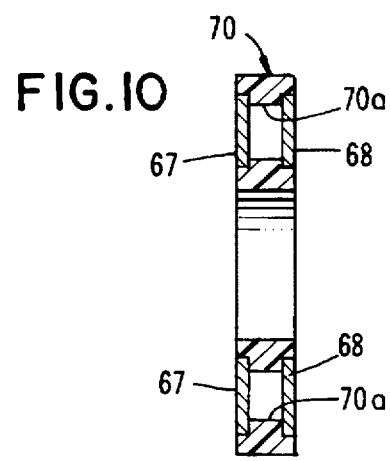
FIG. 10 is a side-elevational, cross-sectional view of the fluid flow control assembly of the apparatus.
Figure 11:
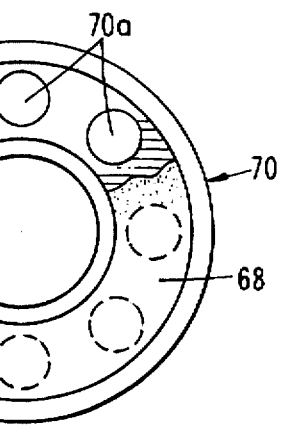
FIG. 11 is a front view of the filter element side of the fluid flow control assembly of the apparatus.

First end 62a of the container is closed by a fill and dispensing means shown here as a head assembly generally designated by the numeral 64. As best seen in FIG. 7, head assembly 64 is of a slightly different construction than the previously described fill and dispensing head and includes a closure cap 66 which is receivable over end 62a of container 62 in the manner shown in FIG. 12. Disposed within cap 66 is a flow control means for controlling the outward flow of fluid flowing from the reservoir or internal chamber 62c of container 62. The flow control means of this embodiment of the invention comprises a generally annular shaped flow rate control element 67 and a generally annular shaped filter element 68. The flow control means further includes a support member 70 which is disposed between, and provides support to, rate control element 67 and filter element 68. As shown in FIG. 10, support member 70 is provided with a plurality of circumferentially spaced fluid flow passageways 70a.

Cap 66 is provided with an annular shaped fluid collection channel 72 which is in communication with passageway 70a and also with the outlet port 73 of the device. Connected to cap 66 proximate outlet port 73 is a hollow infusion needle 74 which is protectively surrounded by an integrally molded twist off cap 75 and a closely fitting closure sleeve 77, which cooperate to maintain the needle in a sterile condition and prevent fluid flow until time of use.

Disposed within chamber 62c of the container is the important stored energy means of the invention, which functions to urge fluid contained within reservoir 62c outwardly of the device via the flow control means and infusion needle 74. This unique stored energy means here comprises a specially configured sponge like member 78 which is movable from a first configuration shown in FIG. 12 to a second, more compressed configuration shown in FIG. 13 wherein it has a tendency to return toward its first configuration.

As previously discussed, the stored energy means, including the stored energy means of this latest embodiment of the invention, can be constructed from a wide variety of materials including rubbers, plastics and other thermoplastic elastomers (TPE) and thermoplastic urethane (TPU).

In operating the apparatus of the form of the invention shown in FIGS. 6 through 13, with the fluid passageway of needle 74 closed by closure sleeve 77, reservoir 62c is filled with the fluid to be dispensed using a syringe having a needle adapted to penetrate a centrally disposed, penetrable septum 80 which is mounted within a central bore 66a provided in cap 66.

As the fluid under pressure flowing from the filling syringe (not shown) enters reservoir 62c, it will engage a piston-like member 82 which is telescopically movable longitudinally of reservoir 62c. This fluid under pressure will urge member 82 telescopically inward of the reservoir causing the stored energy member to be compressed in the manner indicated in FIG. 13.

Figure 13A:
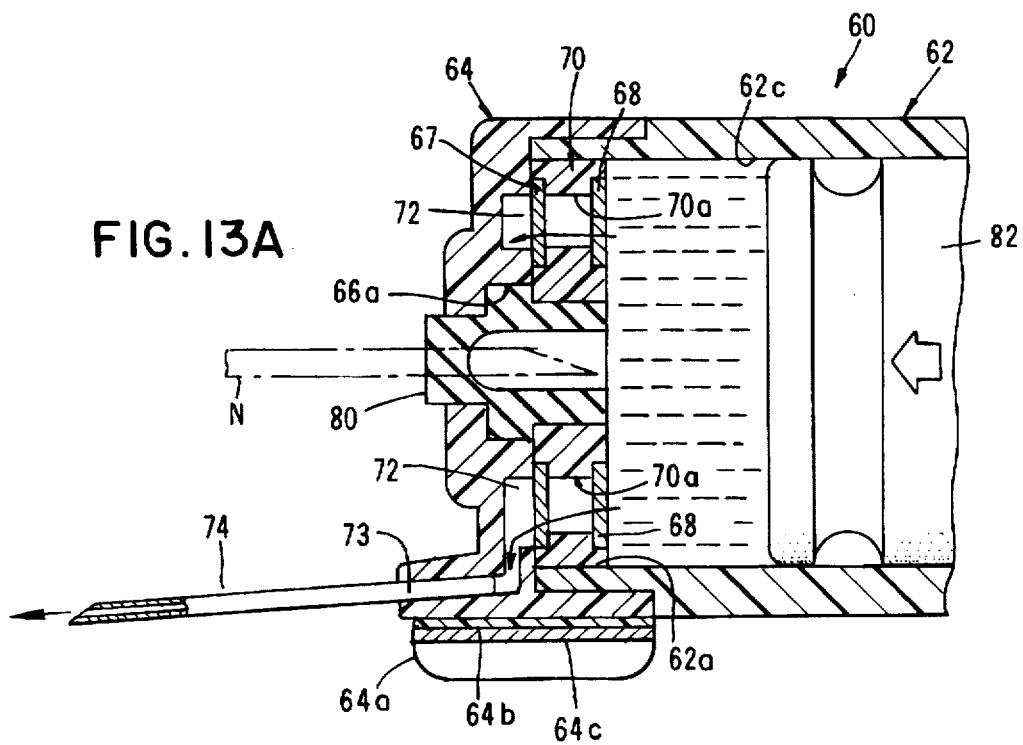
FIG. 13A is a fragmentary, side-elevational view of the forward portion of the device as it appears during the fluid dispensing step.

Upon removing twist off cap 75 and closure sleeve 77 from the needle thereby opening the fluid delivery path of the device, stored energy member 78 will tend to return to its uncompressed, starting configuration thereby controllably urging fluid flow outwardly of reservoir 62c via filter element 68 and rate control element 67. Fluid flowing through these elements will next flow into annular shaped fluid passageway 72 and then outwardly of the device through infusion needle 74. Filter 68 which functions to filter particulate matter from the fluid flowing outwardly from reservoir 62c is of the character previously described herein as is rate control element 67. As before, the various fluids previously identified herein can be dispensed from reservoir 62c. During the delivery step, the infusion needle is, of course, inserted into the vein of the patient. To stabilize the device, cap assembly 64 includes a curved base portion 64a which can be affixed to the patient by an adhesive layer 64b which is protected prior to use by a peal strip 64c (FIG. 13A)

Figure 15:
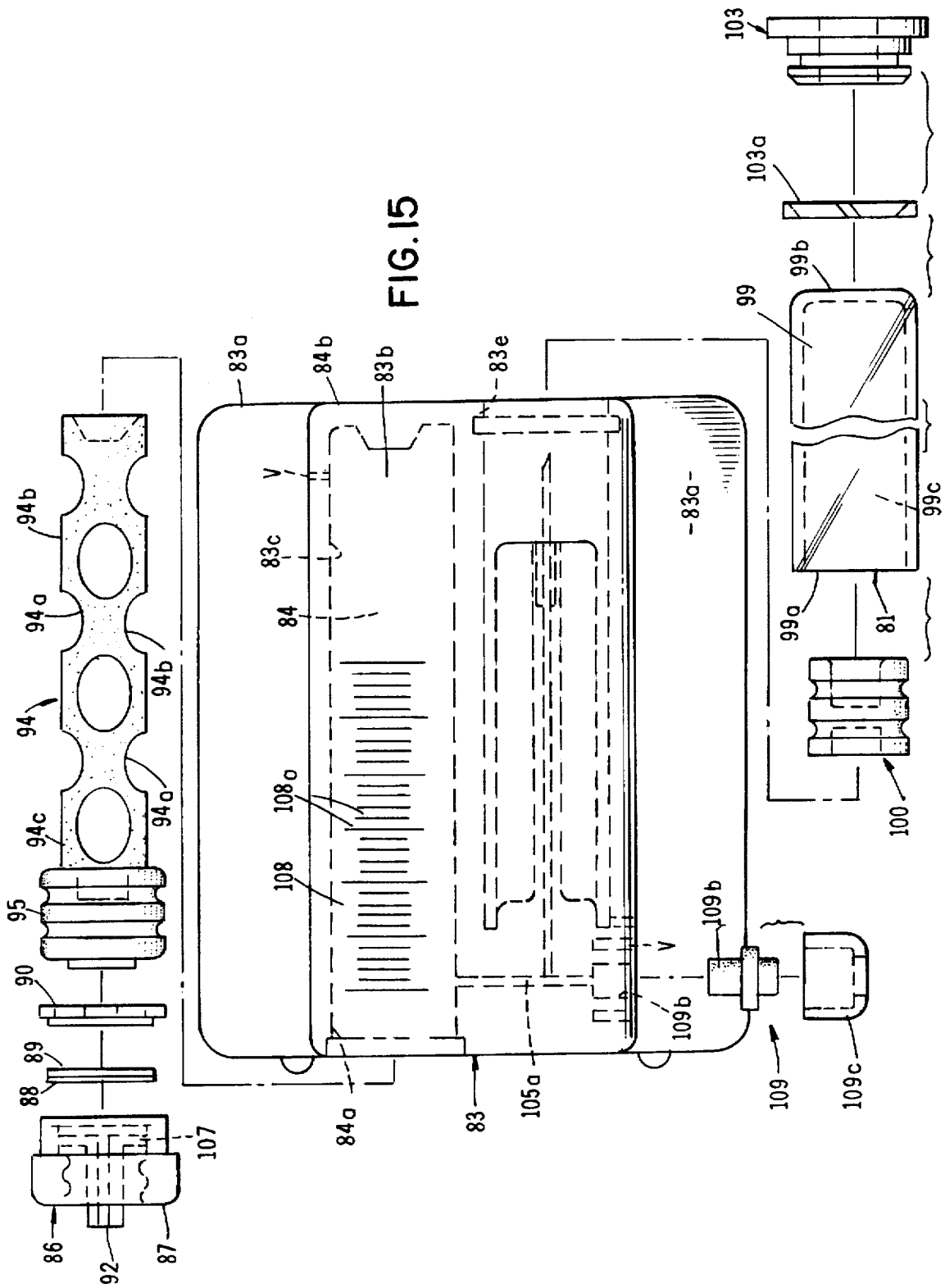
FIG. 15 is a top plan, exploded view of the housing of the apparatus partly broken away to show internal construction, and of the fluid expelling and fluid filling subassemblies of the apparatus.
Figure 17A:
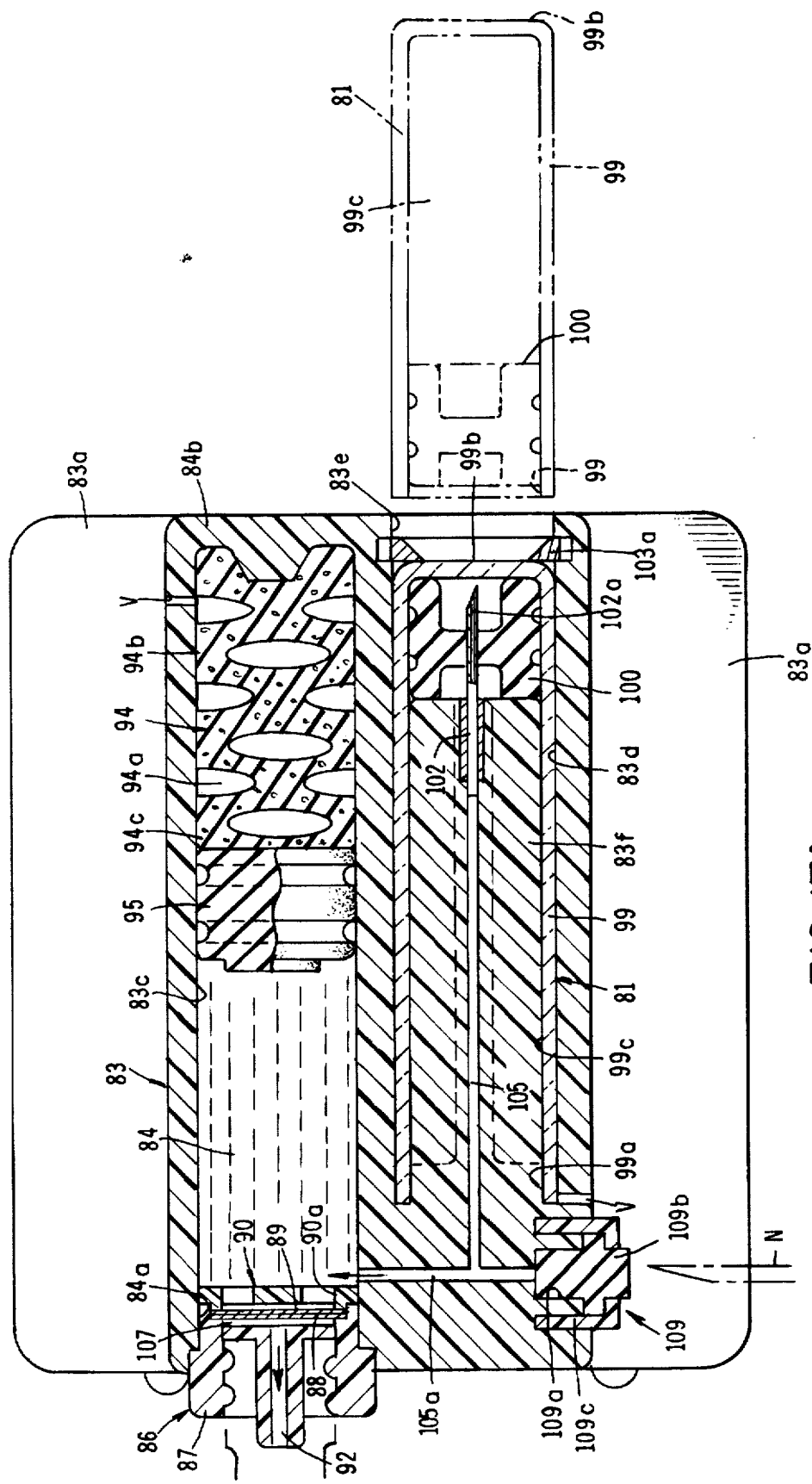
FIG. 17A is a cross-sectional view taken along lines 17A—17A of FIG. 16.

Turning now to FIGS. 14 through 17A, yet another embodiment of the invention is there shown. The dispensing means of this embodiment is somewhat similar to that shown in FIGS. 1 through 5, but the fill means of the apparatus is quite different. More particularly, the fill means here comprises a separate fill assembly 81 (FIG. 15), which is insertable into a chamber formed in a housing 83 of novel construction. As best seen in FIGS. 14 and 15, housing 83 includes a base portion 83a and an upper body portion cover 83b having first and second longitudinally extending internal chambers 83c and 83d which are suitably vented to atmosphere by vents "V". Formed within chamber 83c is a fluid reservoir 84 having a first open end 84a and a closed second end 84b (FIG. 17A). First end 84a is closed by a closure cap assembly 86 of the character shown in FIGS. 14, 15, and 17, which assembly comprises a part of the dispensing means of this embodiment of the invention.

Cap assembly 86 includes a hollow cap 87 which carries the flow control means of this form of the invention for controlling the flow of fluid outwardly of reservoir 84. The flow control means here comprises a generally disc shaped flow rate control wafer 88 and a generally disc shaped filter wafer 89 which are supported in a back-to-back relationship by an apertured support member 90. As shown in FIG. 17, member 90 is provided with a plurality of circumferentially spaced flow passageways 90a to permit fluid flow toward the laminate assemblage made up of wafers 88 and 89.

In this latest form of the invention, cap 87 includes a plurality of radially extending support ribs 87a for supporting the flow control means. Cap 87 also includes a centrally disposed outlet, or fluid delivery port 92, to which a suitable delivery tube (not shown) can be connected (FIG. 17). The flow control means here operates in the same manner to accomplish the same result as does the flow control means considered in connection with the earlier described embodiments of the invention.

Disposed within reservoir 84 is the important stored energy means of the invention, which functions to urge fluid contained within the reservoir outwardly of the device via the flow control means and delivery port 92. This unique stored energy means here comprises a specially configured elastomeric spring-like member 94 which is movable from a first expanded configuration shown in FIG. 15 to a second, more compressed configuration shown in FIG. 17A wherein it has a tendency to return toward its first configuration. As best seen in FIG. 15, member 94 comprises an elongated body having a plurality of longitudinally spaced apart grooves and ridges 94a and 94b respectively. Once again, the stored energy means can be constructed from a wide variety of materials including rubbers, plastics and other thermoplastic elastomers (TPE) and thermoplastic urethane (TPU). The forward end 94c of member 94 engages a piston-like member 95 which is telescopically movable within chamber 83c of body 83.

Receivable within the second longitudinally extending chamber 83d of housing 83 is the previously mentioned fill means of the invention. This novel fill means includes fill vial assembly 81 which comprises a fill vial 99 having a first open end 99a and a second closed end 99b. Fill vial 99 also includes fluid reservoir 99c within which a plunger-like member 100 is telescopically movable from a first position to a second position. Plunger 100, which is constructed of a non-coring elastomer, is adapted to be pierced by an elongated hollow needle 102 which extends longitudinally of chamber 83d of housing 83 in the manner shown in FIG. 17A.

In operating the apparatus of the form of the invention shown in FIGS. 14 through 17A, with the outlet port of the device closed as, for example, by a clamped delivery tube, reservoir 84 can be filled by removing sterile safety cap 103 (FIG. 15) and inserting vial 99 into opening 83e of chamber 83d of housing 83. As the vial, which has been previously prefilled with the fluid to be dispensed, is urged inwardly of chamber 83d, needle 102 will pierce pierceable plunger 100 in the manner shown in FIG. 17A. Continued inward movement of the vial will cause the plunger to engage an internal stem 83f which is formed internally of chamber 83. Stem 83f will force plunger 100 inwardly of the vial from the position shown in the phantom lines of FIG. 17A to the position shown in the solid lines. This telescopic movement of plunger 100 will cause the fluid contained within reservoir 99c to be forced into the internal fluid passageway 102a of hollow needle 102. As best seen in FIG. 15, passageway 102a of the needle communicates with passageway 105 formed in stem 83f and then into a transverse passageway 105a formed internally of housing 83. Passageway 105a is, in turn, in communication with reservoir 84 so that fluid flowing from vial 99 will flow into and fill reservoir 84.

As the fluid under pressure flows into reservoir 84, it will engage a piston-like member 95 which will, in turn, compress stored energy member 94 in the manner shown in FIG. 17A. When vial 99 is fully seated within chamber 83d, a cooperating split ring 103a (FIG. 15) will securely lock the vial in place within chamber 83d in the manner shown in FIG. 17a.

Upon opening the clamped fluid delivery tube, the stored energy means or member 94, will tend to return to its uncompressed starting configuration thereby controllably urging piston 95 to move telescopically within reservoir 84 this telescopic movement of piston 95 will cause the fluid contained in the reservoir to flow outwardly of the device via rate control element 88 and filter element 89. Fluid flowing through these elements will flow into an annular shaped fluid passageway 107 formed in cap assembly 86 and then outwardly of the device via outlet port 92.

Turning once again to FIGS. 14 and 15, it is to be observed that body portion 83b of the housing is provided with a transparent indicia carrying portion 108 which comprises a part of the indicator means of the invention for indicating the amount of fluid contained within reservoir 84. Since reservoir 84 is visible through cover portion 108, the location of member 95 within reservoir 84 can be observed in relation to the indicia 108a provided on portion 108. In this way, at any point in time, the amount of fluid remaining within the reservoir can be readily ascertained.

An alternate filling and drug recovery means for either filling reservoir 84 or for recovering drugs therefrom is also here provided. This alternate means comprises a septum assembly 109 which is carried within a septum receiving chamber 109a provided in the side wall of cover 83b (FIGS. 14 and 15). Chamber 109a is in communication with passageway 105a of housing 83b so that fluid under pressure introduced into passageway 105a through the use of a syringe, the needle of which has pierced septum 109b of the septum assembly, will flow under pressure into reservoir 84. As before, this fluid flowing into reservoir 84 will impinge upon piston 95 moving it telescopically inwardly of the reservoir and controllably compressing the stored energy member 94. After being thusly compressed, the stored energy member can function to controllably expel fluid from the device during the delivery step. In similar fashion, drugs can be removed from the reservoir using a syringe and thereby recovered if desired. As shown in FIG. 15, septum 109b is retained within chamber 109a by a retaining cap 109c which is appropriately bonded to cover 83b (FIG. 17A).

Comprising a part of the housing assembly is means for affixing the device to the patient. This means here comprises a sponge pad 110 having adhesive covered surfaces 110a and 110b (FIG. 14). Pad 110 is receivable within an opening 111 formed in base 83a so that the adhesive covered sponge can bond the cover assembly to base 83 and also bond the assemblage to the patient.

The housing assembly itself can be constructed from various materials including polycarbonate, acrylicf polystyrene and the like. Vial 99 is preferably constructed from glass or suitable plastic materials. Plunger 100 can be constructed from appropriate elastomers such as rubber or silicon.

Needle 102a is preferably made from stainless steel and may be a sharp or blunt end cannula.

Referring next to FIGS. 18 through 33, still another embodiment of the medicament delivery system of the present invention is there illustrated and generally designated by the numeral 112. The apparatus of this form of the invention comprises an elongated body 114, which is made up of three interconnected, generally tubular shaped portions 116, 118, and 120 respectively, portion 120 comprises a part of the operating means of the invention, the purpose of which will presently be described. As best seen by referring to FIG. 23, when portions 116, 118, and 120 are interconnected to form elongated body 114 they define first, second and third communicating interior chambers 122, 124, and 126 respectively.

Removably receivable within a top opening 122a of first chamber 122 (FIG. 21) is a prefilled medicament vial 130 having a first end 130a sealed by a pierceable member 132 and a second end 130b sealed by an elastomeric plunger 134 which is telescopically movable longitudinally of the internal fluid reservoir or chamber 130c of vial 130. Pierceable member 132 comprises a part of the outlet means of the reservoir for permitting fluid flow therefrom.

Disposed within second chamber 124 of elongated body 114 is plunger engaging means for moving plunger 134 of the vial assembly axially of chamber 130c. The details of construction and operation of this plunger engaging means and its interrelationship with the operating means will presently be described. Also disposed within second chamber 124 of the elongated body is the novel stored energy means of the invention, which provides energy necessary to move plunger 134 longitudinally of reservoir 130c. This unique stored energy means here comprises a controllably stretchable elastomeric, dome-like member 137 which is stretchable from a first configuration shown in FIG. 23 to a second, stretched configuration shown in FIG. 33 wherein it has a tendency to return toward its first configuration. The method and apparatus for controllably stretching elastomeric member 137, which includes member 120 and its finger-engaging portion 120a (FIG. 18), will be described in the paragraphs which follow.

Also comprising an important aspect of the apparatus of the present form of the invention is flow control means for controlling the outward flow of fluid flowing from the reservoir or internal chamber 130c of vial 130. This flow control means here comprises a body portion provided in the form of an end cap assembly 140 which is threadably interconnectable with body portion 116. As best seen by referring to FIG. 21, cap assembly 140 comprises an internally threaded cap 142 having a fluid outlet 144 and defining an interior chamber 146. Disposed within chamber 146 and forming a part of the flow control means of the invention is a cannula assembly 148 which comprises a hollow cannula 150 and a cannula support plate 152. Cannula 150 can be either a conventional, sharp, hollow needle or a blunt end cannula of a character well known in the art. Cannula assembly 148 is held in position within cap 142 by sonic bonding or the like. Disposed adjacent plate 152 is a spacer means, shown here as a compressible, elastomeric spacer plug assembly 154, which includes a pierceable membrane 154a that is receivable within the mouth of cap chamber 146 in the manner shown in FIG. 23. Prior to the cap assembly being interconnected with body portion 116 interior chamber 146 of the cap assembly is preferably closed and maintained in a sterile configuration by a tear-away cap of construction well known to those skilled in the art.

Disposed between cannula support plate 152 and an end wall 142a of cap 142 (FIG. 23) is a filtering and flow rate control means for filtering and controlling the rate of fluid flow outwardly through outlet 144 of cap 142. This filtering and fluid rate control means comprises a part of the fluid flow control means of the invention and, in the form of the invention shown in the drawings, includes a rate control filter 161. Rate control 161, which can be constructed from any suitable porous material such as a polycarbonate, a metal or a ceramic, is supported by a support plate 163 carried within chamber 146. In some instances, additional filtration is desired upstream of rate control element 161 and in those instances a porous filter is placed upstream of element 161. This filter can be of the character shown in FIG. 15 and designated by the numeral 89. Support plate 163 can be constructed from any suitable porous material of a character well known by those skilled in the art as, by way of example, porous polypropylene, porous polycarbonate, and porous polysulfone and non-porous polyamide sold under the name and style KAPTON.

Figure 23:
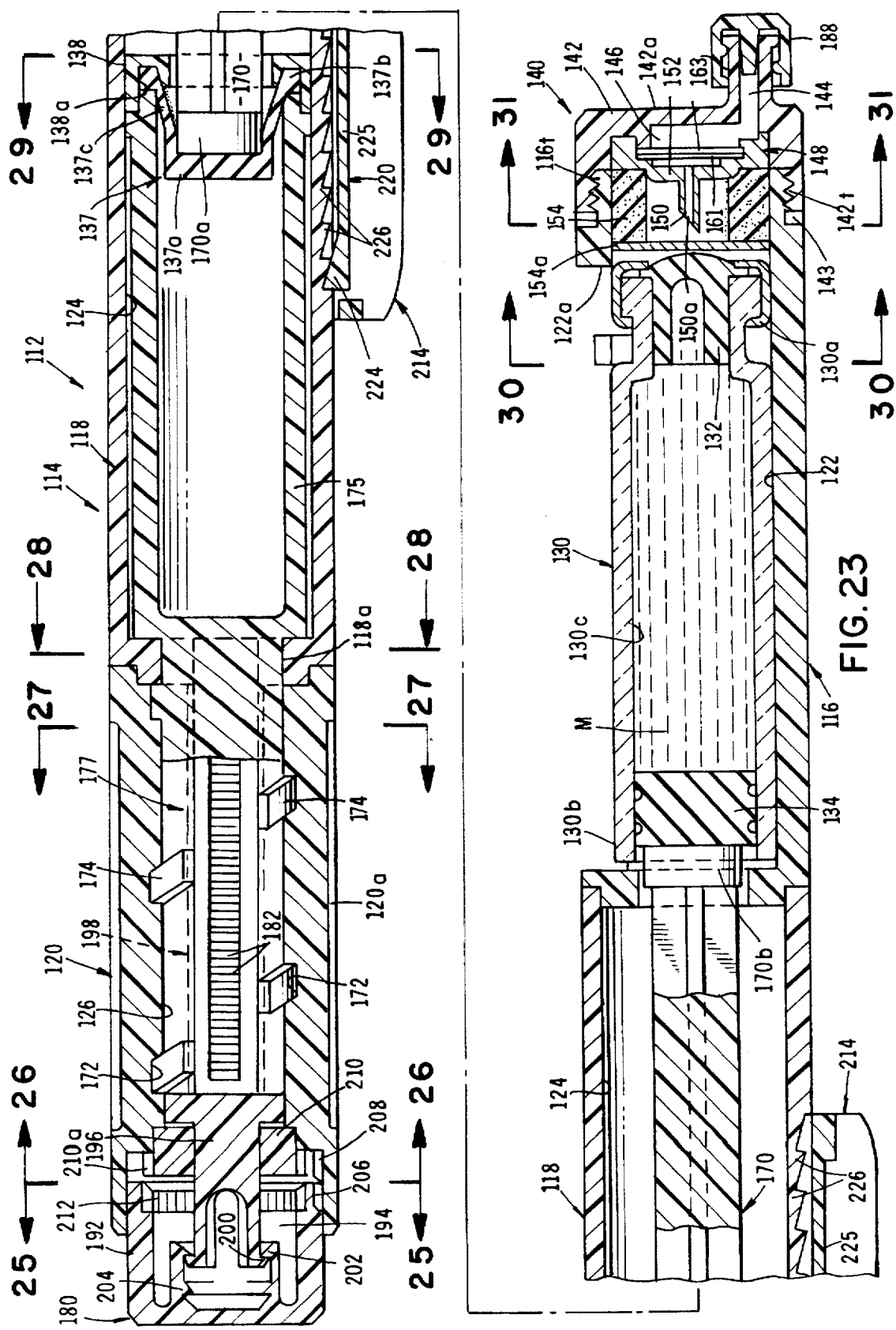
FIG. 23 is an enlarged, cross-sectional view taken along lines 23—23 of FIG. 22.

In using the apparatus of the invention shown in FIGS. 18 through 30 the component parts of the apparatus are assembled in the manner shown in FIG. 23. More particularly, fluid vial 130 containing a fluid such as the medicament "M", which may be insulin, antibiotics, analgesics, oncolytics, human growth hormones, genetically engineered biologic agents, or any other type of injectable beneficial agent, is inserted into first chamber 122 of the elongated body via top opening 122a. End assembly 142 is then threadably interconnected with body portion 116. Next the plunger engaging means shown here as an elongated pusher member 170 is inserted into second chamber 124 in the manner shown in FIG. 23. Connected to pusher member 170 is the novel stored energy means of the invention which is shown here as elastomeric dome member 137. Dome member 137 includes a dome or top portion 137a, a flange 137b and side walls 137c which interconnect portions 137a and 137b. Flange 137b is clamped within a groove 138a formed in a ring 138 which is slidably disposed within chamber 124 by a cylindrical portion 175 of the operating means which also extends into chamber 124. In this regard, it is to be noted that body 120 is provided with internal threads 172 (FIG. 23) which engage external threads 174 that are formed on portion 177 of the operating means which is connected to cylindrical portion 175. Portion 177 is initially disposed within chamber 126 so that as portion 120 is rotated, it cooperates with threaded portion 177 to strategically advance portion 175 inwardly of chamber 124 causing telescopic movement of ring 138 longitudinally of chamber 124.

After the apparatus has been assembled in the manner shown in FIG. 23, a cylindrically shaped head portion 170a of pusher member 170 will engage portion 137a of elastomeric dome 137. Simultaneously, end 170b of the push rod will engage plunger 134 of the vial assembly in the manner shown in FIG. 23. With this novel construction, and unlike the prior art devices, the stored energy means never contacts the fluid to be dispensed thereby preserving the sterile integrity of the reservoir contents.

At the start of the operation of the apparatus of this latest form of the invention, locking means, shown here as a push button assembly 180, is in the unlocked configuration shown in FIG. 23. With the locking means in this unlocked position, rotation of member 120 relative to member 118 and relative to portion 177 will cause portion 177 to advance within chamber 124 from the starting position shown in FIG. 23 to the extended position shown in FIG. 33.

As best seen in FIGS. 21, 23, 24, and 33, portion 177 includes a plurality of longitudinally spaced splines 182 which, during operation of the device, are sequentially engaged by an interiorly extending tab 183 (FIGS. 21 and 24) provided on a forwardly extending portion 198 of member 118. Splines 182 and tab 183 comprise the tactile sensing means of the invention for providing a tactile sensation as the stored energy means is stretched. It is also to be noted that portion 198 includes a bearing surface 118a upon which member 120 rotates.

As portion 177 of the operating means moves toward its advanced or extended position, it will urge travel of ring 138 over pusher member 170. However, when the outlet port of cap 140 is closed by closure 188 in the manner shown in FIG. 23, fluid cannot flow outwardly of the outlet port. Accordingly, when the outlet is closed, the resistance offered by the fluid within the vial reservoir to axial movement of plunger 134 will cause the pusher member to controllably stretch wall 137c of elastomeric dome 137 in the manner shown in FIG. 33. With this construction, upon opening outlet 144, only then will a fluid flow path be formed between the medicament reservoir of the vial and an infusion set or other delivery system 190 which is connected to cap 142 in the manner shown in FIG. 34, thereby permitting fluid to be dispensed from the device. As before, expansion of the stored energy means provides the force necessary to cause the controlled movement of the vial plunger and the resulting discharge of the fluid contained within the vial. It is to be noted that a novel feature of the operating means is that this means permits the stored energy means to be controllably expanded to any desired strain energy density loading to enable precise solution of fluid flow rates. Indicia "I" are provided on members 118 and 120 so that the degree of loading of the stored energy means can be selected.

Figure 21:
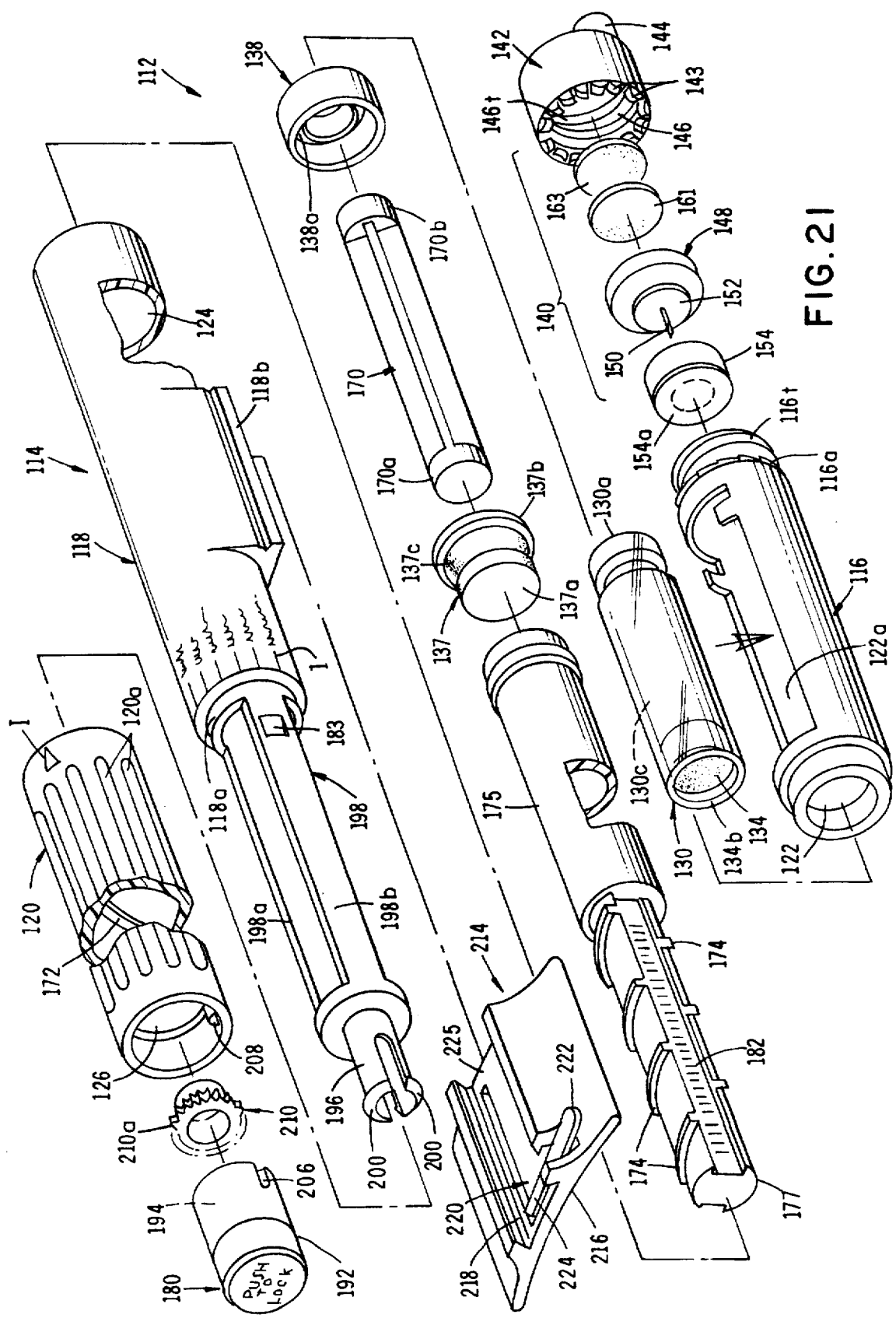
FIG. 21 is a generally perspective, exploded view of the apparatus of the invention shown in FIG. 18.

Following the desired strain energy density loading of the stored energy means, portion 177 of the operating means can be locked in the extended position shown in FIG. 33 through operation of push button 192 of the locking means or locking assembly 180 in a manner to push it inwardly into the open end of body portion 120. As best seen by referring to FIGS. 21 and 23, push button 192 includes an internal chamber 194 into which a generally cylindrically shaped extension 196 of portion 198 of member 118 extends. As best seen in FIG. 21, portion 198 comprises a pair of spaced apart connector arms 198a and 198b which connect portions 118a and 196.

Formed on extension 196 are circumferentially spaced, arcuate shaped retaining segments 200 (FIG. 21) which are lockably engageable with a first annular collar 202 formed within chamber 194. Also formed within chamber 194 is a second annular collar 204 which is engageable by arcuate retaining segments 200 when push button 192 is pushed inwardly of body portion 120 (FIG. 33). To guide travel of push button 192 inwardly of body portion 120 and to lock the finger-engaging means against rotation with respect to member 118, the push button is provided with a keyway 206 (FIGS. 21 and 23) which slidably receives a key 208 formed within interior chamber 126 of body portion 120. Also forming a part of the locking means of this form of the invention, is a non-rotatable locking ring 210 which is affixed to extension 196 as by sonic bonding. As indicated in FIG. 21, ring 210 is provided with circumferentially extending teeth 210a which lockably engage serations 212 provided within push button 192 when the push button is fully inserted as shown in FIG. 33. Because key 208 is locked within keyway 206, rotation of the push button relative to the member 120 is prevented. Therefore, when the push button is locked against rotation with respect to fixed ring 210, rotation of member 120 is also positively prevented.

During the fluid delivery step, the stored energy source or stretched elastomeric dome member 137, will move pusher member 170 toward its initial starting configuration. This causes vial 130 to move from the position shown in FIG. 23 to the position shown in FIG. 33 wherein cannula 150 pierces member 154a and septum 132 thereby opening a flow path between reservoir 130c and the fluid delivery means. The stored energy source will then cause plunger 134 to move axially of reservoir 130c from a first position shown in FIG. 23 to a second position shown in FIG. 34. As the plunger moves within the reservoir, the fluid contained therein will be urged into the fluid passageway 150 of cannula 150 and toward the flow control means of the apparatus (FIG. 34). The fluid will then flow under pressure through rate control 161 and then outwardly of outlet 144 and into the fluid delivery means 190.

The various fluids that can be dispensed from vial 130c, include all those previously described, including by way of example, beneficial agents, such as medicaments of various types, drugs and pharmaceuticals.

With respect to the important stored energy means, as before a wide variety of materials such as those previously described, can be used to form the stored energy means including synthetic polymers, latex rubber, synthetic rubber, rubber polyolefins, silicon plastics and other thermoplastic elastomers (TPE) and thermoplastic urethane (TPU).

Manufactures of materials suitable for use in the construction of stored energy source, include Advance Elastomer Systems, Dow Chemical, General Electric, B.P. Polymers, Mobay Chemical, Shell Oil Corp., Petrarch Systems, DuPont, Akron Rubber, Concept Polymers and Union Carbide.

Turning particularly to FIGS. 21, 31, and 32 cap 142 is provided with threads 142t which threadably engage threads 116t provided on body portion 116. Cap 142 is also provided with circumferentially extending, flexibly deformable locking tabs 143 which are adapted to lockably engage locking teeth 116a provided on body portion 116. When the locking tabs 143 engage locking teeth 116a in the manner shown in FIG. 32, removal of the cap is effectively prevented.

Turning next to FIGS. 18, 21, 22, and 29, the embodiment of the invention there shown comprises a support means for removably supporting body 114. This support means here includes a supporting base assembly 214, which is designed to be lockably interconnected with and securely support elongated body 118 in the manner shown in FIG. 18. As best seen in FIG. 21, base assembly 214 includes a curved base plate 216 which is provided with longitudinally extending channel 218 and a locking assembly 220 which includes a transversely extending release arm 222 having a locking protuberance 224. Locking protuberance 224 is provided with a sloping face that is adapted to engage one of a plurality of outwardly extending locking teeth 226 (FIG. 23) provided on the base of body member 118 as flange portion 118b of member 118 is slidably received within groove 218.

With this construction, as flange 118b slides into groove 218 protuberance 224 will ratchet over teeth 226 until body portion 118 is finally seated within the base assembly. At this point, the engaged tooth will block removal of flange 118b. However, upon depressing arm 222, protuberance 224 will pivot downwardly about leg 225 (FIG. 21) of the release mechanism so as to move clear of the teeth so that body portion 118 can be disengaged from the base assembly.

Body 114 can be interconnected with other types of base assemblies which permit the interconnection therewith of a variety of fastening devices that enable the apparatus to be readily interconnected with the body or clothing of an ambulatory patient.

Materials particularly well suited for the construction of the elongated body and the operating member include polycarbonates, nylons, and acrylics. Preferred materials for the construction of the pusher-engaging member include polypropylene, polystyrene and polyoxnyl chloride.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dispensing apparatus for dispensing fluids comprising:
   (a) a container;
   (b) a fluid reservoir disposed within said container, said reservoir having an outlet for permitting fluid flow from said fluid reservoir;
   (c) a plunger sealably movable within said reservoir from a first position to a second position;

(d) stored energy means for acting upon said plunger to cause the fluid to controllably flow through said outlet means, said stored energy means comprising a compressively deformable, elastomeric member carried within said reservoir, said compressively deformable elastomeric member being expandable to cause fluid flow from said reservoir; and (e) fill means operatively associated with said container for filling said reservoir with the fluid to be dispensed and to cause said stored energy means to compressively deform.

2. An apparatus as defined in claim 1 further including flow control means operatively associated with said container for controlling fluid flowing from said outlet means of said reservoir.

3. An apparatus as defined in claim 1 in which said elastomeric member comprises a flexible polymeric member.

4. An apparatus as defined in claim 1 in which said elastomeric member comprises a cellular mass.

5. An apparatus as defined in claim 1 in which said container comprises a vial having a first open end and a closed second end, said reservior being disposed between said first and second ends.

6. An apparatus as defined in claim 5 in which said fill means comprises a closure cap connected to said first end of said vial, said closure cap having a fluid outlet.

7. An apparatus as defined in claim 6 in which said flow control means comprises a flow rate control element carried within said closure cap.

8. An apparatus as defined in claim 6 in which said flow control means comprises a filter element carried within said closure cap.

9. An apparatus as defined in claim 6 further including a fluid administration line with luer connector disposed in fluid communication with said fluid outlet.

10. A dispensing device for dispensing fluid comprising:

(a) a container having a first open end and a closed second end and a fluid reservoir disposed between first and second ends;

(b) a fill and dispensing means connected to said first end of said container for filling said fluid reservoir with the fluid to be dispensed and for dispensing the fluid from said reservoir, said fill and dispensing means comprising a closure cap having a fluid outlet; and (c) stored energy means disposed within one of said fluid reservoir for acting upon the fluid contained therein to cause the fluid to controllably flow through said fluid outlet of said closure cap, said stored energy means comprising a compressively deformable, elastomeric member, said compressively deformable, elastomeric member being compressively deformed by the fluid filling said fluid reservoir and being expandable to cause fluid flow from said reservoir toward said fluid outlet.

11. An apparatus as defined in claim 10 in which said elastomeric member comprises a flexible polymeric member.

12. An apparatus as defined in claim 10 further including flow control means carried by said closure cap for controlling fluid flow between said reservoir and said fluid outlet.

13. An apparatus as defined in claim 12 in which said flow control means comprises fluid flow rate control means for controlling the rate of the fluid flow from said reservoir toward said fluid outlet.

14. An apparatus as defined in claim 12 in which said flow control means comprises filter means for filtering particulate matter from fluid flowing from said reservoir.

15. An apparatus as defined in claim 1 in which said closure cap includes a central bore defining a valve seat and in which said valve means comprises a valve member movable within said bore toward and away from said valve seat.

16. An apparatus as defined in claim 15 in which said closure cap includes a luer connector and in which said apparatus further includes a filling assembly interconnectable with said luer connector.

17. A dispensing device for dispensing fluid comprising:

(a) a container having a first open end and a closed second end and a fluid reservoir disposed between first and second ends;

(b) a fill and dispensing means connected to said first end of said container for filling said fluid reservoir with the fluid to be dispensed and for dispensing the fluid from said reservoir, said fill and dispensing means comprising a closure cap having a fluid outlet; and (c) stored energy means disposed within one of said fluid reservoir for acting upon the fluid contained therein to cause the fluid to controllably flow through said fluid outlet of said closure cap, said stored energy means comprising a compressively deformable, elastomeric member, said compressively deformable, elastomeric member being expandable to cause fluid flow from said reservoir toward said fluid outlet.

(d) flow control means carried by said closure cap for controlling fluid flow between said reservoir and said fluid outlet, said flow control means comprising valve means for blocking fluid flow between said reservoir and said fluid outlet.

* * * * *